US009011864B2

(12) United States Patent
Schulz et al.

(10) Patent No.: US 9,011,864 B2
(45) Date of Patent: Apr. 21, 2015

(54) METHOD OF DECREASING CYTOTOXIC SIDE-EFFECTS AND IMPROVING EFFICACY OF IMMUNOCONJUGATES

(75) Inventors: Gregor Schulz, Umkirch (DE); Christoph Bruecher, Eschborn (DE); Frank Osterroth, Dietzenbach (DE); Steffen Zeng, Muenster (DE); Christoph Uherek, Seligenstadt (DE); Silke Aigner, Frankenthal (DE); Benjamin Daelken, Frankfurt am Main (DE); Markus Ruehle, Wiesbaden (DE); Elmar Kraus, Bad Vilbel (DE)

(73) Assignees: Biotest AG, Dreieich (DE); Immunogen, Inc., Waltham, MA (US)

( * ) Notice: Subject to any disclaimer, the term of this patent is extended or adjusted under 35 U.S.C. 154(b) by 0 days.

(21) Appl. No.: 12/342,180

(22) Filed: Dec. 23, 2008

(65) Prior Publication Data

US 2009/0181038 A1 Jul. 16, 2009

Related U.S. Application Data

(60) Provisional application No. 61/016,613, filed on Dec. 26, 2007, provisional application No. 61/016,630, filed on Dec. 26, 2007.

(51) Int. Cl.
*A61K 39/00* (2006.01)
*A61K 39/395* (2006.01)
*A61K 47/48* (2006.01)
*C07K 16/28* (2006.01)
*B82Y 5/00* (2011.01)

(52) U.S. Cl.
CPC ....... *C07K 16/2896* (2013.01); *A61K 47/48561* (2013.01); *A61K 2039/505* (2013.01); *A61K 39/39558* (2013.01); *C07K 2317/34* (2013.01); *B82Y 5/00* (2013.01); *A61K 47/48723* (2013.01); *C07K 2317/24* (2013.01); *A61K 47/48569* (2013.01)
USPC .................. 424/178.1; 424/130.1; 424/133.1; 424/138.1; 424/139.1; 424/141.1; 424/155.1

(58) Field of Classification Search
None
See application file for complete search history.

(56) References Cited

U.S. PATENT DOCUMENTS

| | | | |
|---|---|---|---|
| 3,896,111 A | 7/1975 | Kupchan et al. | |
| 4,137,230 A | 1/1979 | Hashimoto et al. | |
| 4,151,042 A | 4/1979 | Higashide et al. | |
| 4,169,888 A | 10/1979 | Hanka et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,418,064 A | 11/1983 | Powell et al. | |
| 4,424,219 A | 1/1984 | Hashimoto et al. | |
| 4,444,887 A | 4/1984 | Hoffmann | |
| 4,761,111 A | 8/1988 | Brown | |
| 5,034,223 A * | 7/1991 | Abrams et al. | 424/1.49 |
| 5,053,394 A | 10/1991 | Ellestad et al. | |
| 5,208,020 A | 5/1993 | Chari et al. | |
| 5,367,086 A | 11/1994 | Rao | |
| 5,475,092 A | 12/1995 | Chari et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,585,089 A | 12/1996 | Queen et al. | |
| 5,585,499 A | 12/1996 | Chari et al. | |
| 5,612,016 A * | 3/1997 | Griffiths et al. | 424/1.49 |
| 5,639,641 A | 6/1997 | Pedersen et al. | |

(Continued)

FOREIGN PATENT DOCUMENTS

EP 0239400 A2 9/1987
EP 0519596 A1 12/1992

(Continued)

OTHER PUBLICATIONS

Fundamental Immunology, William E. Paul M.D., ed., 3rd Ed., pp. 292-295, 1993.*
Rudikoff et al. Proc. Natl. Acad. Sci. USA, 79(6):1979-1983, Mar. 1982.*
Colman P. M. Research in Immunology, 145:33-36, 1994.*
MacCallum et al. J. Mol. Biol., 262, 732-745, 1996.*
Casset et al. Biochemical and Biophysical Research Communications, 307:198-205, 2003.*
Bendig M. M., Methods: A Companion to Methods in Enzymology, 1995; 8:83-93.*
Fundamental Immunology, (William E. Paul, M.D. ed., 3d ed. 1993), p. 242.*
Buchsbaum, Cancer Res. 1995, 55, suppl., 5729s-5732s.*
Allum et al., J. Clin. Pathol, 1986, 39:610-614.*

(Continued)

*Primary Examiner* — Hong Sang
(74) *Attorney, Agent, or Firm* — Joyce von Natzmer; Agris & von Natzmer LLP

(57) ABSTRACT

Disclosed are methods, compositions and kits for improving targeting, in particular tumor targeting, of immunoconjugates. The method and composition relies on the sequestration of non-target cells that also express the antigen the immunoconjugate targets. Sequestration of those non-target cells in a variety of ways is disclosed. The methods, compositions and kits allow appropriate sequestration of non-target cells while maintaining a high degree of effectiveness of the immunoconjugates against target cells.

18 Claims, 8 Drawing Sheets

(56) References Cited

U.S. PATENT DOCUMENTS

| | | | |
|---|---|---|---|
| 5,703,247 A | 12/1997 | Kingston et al. | |
| 5,705,508 A | 1/1998 | Ojima et al. | |
| 5,712,374 A | 1/1998 | Kuntsmann et al. | |
| 5,714,586 A | 2/1998 | Kunstmann et al. | |
| 5,739,350 A | 4/1998 | Kelly et al. | |
| 5,763,477 A | 6/1998 | Duvvuri et al. | |
| 5,773,001 A | 6/1998 | Hamann et al. | |
| 5,814,318 A | 9/1998 | Lonberg et al. | |
| 5,831,012 A | 11/1998 | Nilsson et al. | |
| 5,846,545 A | 12/1998 | Chari et al. | |
| 5,877,296 A | 3/1999 | Hamann et al. | |
| 5,892,063 A | 4/1999 | Zheng et al. | |
| 5,998,656 A | 12/1999 | Holton et al. | |
| 6,002,023 A | 12/1999 | Kingston et al. | |
| 6,005,079 A | 12/1999 | Casterman et al. | |
| 6,080,777 A | 6/2000 | Schiff | |
| 6,087,362 A * | 7/2000 | El-Rashidy | 514/252.16 |
| 6,333,410 B1 | 12/2001 | Chari et al. | |
| 6,340,701 B1 | 1/2002 | Chari et al. | |
| 6,436,931 B1 | 8/2002 | Chari et al. | |
| 6,534,628 B1 | 3/2003 | Nilsson et al. | |
| 6,534,660 B1 | 3/2003 | Yongxin et al. | |
| 6,596,757 B1 | 7/2003 | Chari et al. | |
| 6,706,708 B2 | 3/2004 | Chari et al. | |
| 6,716,821 B2 | 4/2004 | Zhao et al. | |
| 6,740,734 B1 | 5/2004 | Nilsson et al. | |
| 6,756,397 B2 | 6/2004 | Zhao et al. | |
| 2002/0006379 A1 | 1/2002 | Hansen et al. | |
| 2003/0004210 A1 | 1/2003 | Chari et al. | |
| 2003/0055226 A1 | 3/2003 | Chari et al. | |
| 2004/0024049 A1 | 2/2004 | Baloglu et al. | |
| 2004/0082764 A1 | 4/2004 | Kunz et al. | |
| 2004/0087649 A1 | 5/2004 | Chari et al. | |
| 2004/0126379 A1 | 7/2004 | Adolf et al. | |
| 2004/0235840 A1 | 11/2004 | Chari et al. | |
| 2004/0241817 A1 | 12/2004 | Umana et al. | |
| 2005/0123549 A1 | 6/2005 | Payne et al. | |
| 2005/0271653 A1* | 12/2005 | Strahilevitz | 424/140.1 |
| 2005/0272128 A1 | 12/2005 | Umana et al. | |
| 2006/0045877 A1* | 3/2006 | Goldmakher | 424/133.1 |
| 2006/0233814 A1 | 10/2006 | Goldmakher et al. | |
| 2007/0183971 A1 | 8/2007 | Goldmakher | |
| 2008/0171040 A1 | 7/2008 | Ebens et al. | |

FOREIGN PATENT DOCUMENTS

| | | |
|---|---|---|
| EP | 0592106 A1 | 4/1994 |
| WO | 8802594 A2 | 4/1988 |
| WO | 91/09967 A1 | 7/1991 |
| WO | 91/10741 A1 | 7/1991 |
| WO | 96/33735 A1 | 10/1996 |
| WO | 96/34096 A1 | 10/1996 |
| WO | 98/16654 A1 | 4/1998 |
| WO | 98/24893 A1 | 6/1998 |
| WO | 98/46645 A2 | 10/1998 |
| WO | 98/50433 | 11/1998 |
| WO | 2004099379 | 11/2004 |
| WO | 2006099875 | 9/2006 |
| WO | 2007066109 | 6/2007 |
| WO | 2007144046 | 12/2007 |

OTHER PUBLICATIONS

Akkina et al., "Modeling human lymphoid precursor cell gene therapy in the SCID-hu mouse," Blood, 1994, 84, pp. 1393-1398.

Anttonen et al., "High syndecan-1 expression is associated with favourable outcome in squamous cell lung Carcinoma treated with radical surgery," Lung Cancer, Jun. 2001, 32(3), pp. 297-305.

Barbareschi et al., "High syndecan-1 expression in breast Carcinoma is related to an aggressive phenotype and to poorer prognosis," Cancer, Aug. 1, 2003, 98(3), pp. 474-483.

Bernfield et al., "Biology of the syndecans: a family of transmembrane heparan sulfate proteoglycans," Annu RevCell Biol, 1992, 8, pp: 365-393.

Beste et al., "Small antibody-like proteins with prescribed ligand specificities derived from the lipocalin fold," Proc. Natl. Acad. Sei. USA, 1999, 96, pp. 1898-1903.

Bhattacharyy et al., "Maytansine binding to the vinblastine sites of tubulin," FEBS Lett, 1977, 75, pp. 159-162.

Blattler et al., "Drugs to Enhance the Therapeutic Potency of Anticancer Antibodies: Antibody-Drug Conjugates as Tumor-Activated Prodrugs," Anticancer Agents-Frontiers in Cancer Chemotherapy, American Chemical Society, Washington, DC, 2001, pp. 317-338.

Bross et al., "Approval summary: gemtuzumab ozogamicin in relapsed acute myeloid leukemia," Clin Cancer Res, 2001, 7, pp. 1490-1496.

Carbone et al., "AIDS-related plasma-blastic lymphomas of the oral cavity and jaws: a diagnostic dilemma," Ann. Otol. Rhinol. Laryngol., 1999, 108, pp. 95-99.

Carbone et al., "Reed-Sternberg cells of classical Hodgkin's disease react with the plasma cell-specific monoclonal antibody B-B4 and express human syndecan-1," Blood, 1997, 89, pp. 3787-3794.

Carter P., "Improving the efficacy of antibody-based Cancer therapies," Nat Rev Cancer, 2001, 1, pp. 118-129.

Chari et al., "Goldmacher VS. Immunoconjugates containing novel maytansinoids: promising anticancerdrugs," Cancer Res., 1992, 52, pp. 127-131.

Chari et al., "Goldmacher VS. Enhancement of the selectivity and antitumor efficacy of a CC-1065 analogue through immunoconjugate formation," Cancer Res., 1995, 55, pp. 4079-4084.

Charnaux et al., "RANTES (CCL5) induces a CCR5-dependent accelerated shedding of syndecan-1 (CD138) and syndecan-4 from HeLa cells and forms complexes with the shed ectodomains of these proteoglycans as well as with those of CD44," Glycobiology, 2005, 5(2) pp. 119-130.

Chen et al., "Engraftment of human hematopoietic precursor cells with secondary transfer potential in SCID-hu mice," Blood, 1994, 84, pp. 2497-2505.

Chilosi et al., "CD138/syndecan-1: a useful immunohistochemical marker of normal and neoplastic plasma cells on routine trephine bone marrow biopsies," Mod Pathol., 1999, 12 pp. 1101-1106.

Clement et al., "B-B2 and B-B4: two new mAb against secreting plasma cells," SFSe, ed. J. Leukocyte Typing V. Oxford: Oxford University Press, 1995 pp. 714-715.

Couturier et al., "Validation of 213Bi-alpha radioimmunotherapy for multiple myeloma," Clinical Cancer Research, 5(10 Suppl.), Oct. 1999, pp. 3165s-3170s.

Davies et al., "Distribution and Clinical Significance of Heparan Sulfate Proteoglycans," Ovarian Cancer Clin Cancer Res., 2004, 10(15), pp. 5178-5186.

Dhodapkar et al., "Antitumor monoclonal abs enhance cross-presentation of Cellular antigens and the generation of myeloma-specific killer T cells by dendritic cells," J Exp Med, Jan. 7, 2002, 195(1), pp. 125-133.

Dhodapkar et al., "T cells from the tumor microenvironment of patients with progressive myeloma can generate strong, tumor-specific cytolytic responses to autologous, tumor-loaded dendritic cells," Proc Natl Acad Sci U S A., Oct. 1, 2002, 99(20) pp. 13009-13013, Epub Sep. 16, 2002.

Dhodapkar et al., "Syndecan-1 is a multifunctional regulator of myeloma pathobiology: control of tumor cell survival, growth, and bone cell differentiation," Blood, 1998, 91, pp. 2679-2688.

Dore et al., "Identification and location on syndecan-1 core protein of the epitopes of B-B2 and B-B4 monoclonal antibodies," FEBS Lett., 1998, 426, pp. 67-70.

Dowell et al., "Pharmacokinetics of gemtuzumab ozogamicin, an antibody-targeted chemotherapy agent for the treatment of patients with acute myeloid leukemia in first relapse," J Clin Pharmacol, 2001, 41, pp. 1206-1214.

Edinger et al., "Noninvasive assessment of tumor cell proliferation in animal models," Neoplasia, 1999, 1, pp. 303-310.

Gattei et al., "Characterization of Anti-CD138 monoclonal antibodies as tools for investigating the molecular polymorphism of syndecan-1 in human lymphoma cells," Br J Haematol, 1999, 104, pp. 152-162.

(56) References Cited

OTHER PUBLICATIONS

Hamann et al., "An anti-CD33 antibody-calicheamicin conjugate for treatment of acute myeloid leukemia. Choice of linker," Bioconjug Chem, 2002, 13, pp. 40-46.
Han et al., "New insights into syndecan-2 expression and tumourigenic activity in colon carcinoma cells," J Mol Histol., 2004, 35(3), pp. 319-326.
Horvathova et al., "Identification of novel and specific antigens of human plasma cells by mAb," SFSe, ed. Leucocyte Typing V. Oxford: Oxford University Press, 1995, pp. 713-714.
Jokimaa et al., "Expression of syndecan-1 in human placenta and decidua," Placenta, Mar.-Apr. 1998, 19(2-3), pp. 157-163.
Jokimaa et al., "Placental expression of syndecan 1 is diminished in preeclampsia," Am J Obstet Gynecol, Dec. 2000, 183(6), pp. 1495-1498.
Krebs et al., "High-throughput generation and engineering of recombinant human antibodies," J. Immunol, Methods 254, 2001, pp. 67-84.
Kupchan et al., "Structural requirements for antileukemic activity among the naturally occurring and semisynthetic maytansinoids," J Med Chem, 1978, 21, pp. 31-37.
Kyoizumi et al., "Implantation and maintenance of functional human bone marrow in SCID-hu mice," Blood, 1992, 79, pp. 1704-1711.
Kyoizumi et al., "Preclinical analysis of cytokine therapy in the SCID-hu mouse," Blood, 1993, 81 pp. 1479-1488.
Liu et al., "Eradication of large colon tumor xenografts by targeted delivery of maytansinoids," Proc Natl Acad Sci U S A, 1996, 93, pp. 8618-8623.
McCune et al., "The SCID-hu mouse: murine model for the analysis of human hematolymphoid differentiation and function," Science, 1988, 241, pp. 1632-1639.
Mennerich et al. "Shift of syndecan-1 expression from epithelial to stromal cells during progression of solid tumours," Eur J Cancer, Jun. 2004, 40(9), pp. 1373-1382.
Mosmann T., "Rapid colorimetric assay for cellular growth and survival: application to proliferation and cytotoxicity assays," J Immunol Methods, 1983, 65, pp. 55-63.
Mukunyadzi et al., "The level of syndecan-1 expression is a distinguishing feature in behavior between keratoacanthoma and invasive cutaneous squamous cell carcinoma," Mod Pathol., Jan. 2002, 15(1), pp. 45-49.
Namikawa et al., "Growth of human myeloid leukemias in the human marrow environment of SCID-hu mice," Blood, Oct. 15, 1993, 82(8), pp. 2526-2536.
O'Connell FP et al., "CD138 (Syndecan-1), a Plasma Cell Marker Immunohistochemical Profile in Hematopoietic and Nonhematopoietic Neoplasms," Am J Clin Pathol, 2004, 121, pp. 254-263.
Ojima et al., "Tumor-specific novel taxoid-monoclonal antibody conjugates," 2002, J. Med. Chem., 45, pp. 5620-5623.
Olafsen et al., "Covalent disulfide-linked anti-CEA diabody allows site-specific conjugation and radiolabeling for tumor targeting applications," 2004, Prot. Eng. Design & Selection, 17, 1, pp. 21-27.
Orosz et al., "Syndecan-1 expression in different soft tissue tumours," Anticancer Res., 2001, 21(1B), pp. 733-737.
Padlan, EA, "A possible procedure for reducing the immunogenicity of antibody variable domains while preserving their ligand-binding properties," Mol. Immunol., 1991, 28 pp. 489-498.
Palacios et al., "B-B4 monoclonal antibody and identification of human bone marrow plasma cells (including response)," Br J Haematol, 1997, 96, pp. 654-657.
Payne G., "Progress in immunoconjugate cancer therapeutics," Cancer Cell, 2003, 3, pp. 207-212.
Pegram et al. "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment," 1998, J. Clin. Oncol., 16, pp. 2659-2671.
Post et al., "Efficacy of an anti-CD138 immunotoxin and doxorubicin on drug-resistant and drug-sensitive myeloma cells," Int J Cancer, Nov. 12, 1999, 83(4), pp. 571-576.
Rawstron et al., "Circulating plasma cells in multiple myeloma: characterization and correlation with disease stage," Br J Haematol, 1997, 97, pp. 46-55.
Remillard et al., "Antimitotic activity of the potent tumor inhibitor maytansine," Science, 1975,189, pp. 1002-1005.
Rintala et al., "Association of syndecan-1 with tumor grade and histology in primary invasive cervical carcinoma," Gynecol Oncol, Dec. 1999, 75(3), pp. 372-378.
Roguska et al., "Humanization of murine monoclonal antibodies through variable domain resurfacing," Proc Natl Acad Sci U S A, 1994, 91, pp. 969-973.
Ross et al., "Anticancer Antibodies," Am J Clin Path, 2003, 119, pp. 472-485.
Ross et al., "Prostate stem cell antigen as therapy target: tissue expression and in vivo efficacy of an immunoconjugate," Cancer Res, May 1, 2002, 62(9), pp. 2546-2553.
Sanderson et al., "B lymphocytes express and lose syndecan at specific stages of differentiation," Cell Regul, 1989, 1, pp. 27-35.
Sandhu et al., "Human hematopoiesis in SCID mice implanted with human adult cancellous bone," Blood, 1996, 88, pp. 1973-1982.
Sasaki et al., "Bisphosphonate risedronate reduces metastatic human breast cancer burden in bone in nude mice," Cancer Res, 1995, 55, pp. 3551-3557.
Schneider et al., "Two subsets of peripheral blood plasma cells defined by differential expression of CD45 antigen," Br J Haematol, 1997, 97, pp. 56-64.
Sebestyen et al., "Syndecan-1 (CD138) expression in human non-Hodgkin lymphomas," Br J Haematol, 1999, 104(2), pp. 412-419.
Seftalioglu et al., "Syndecan-1/CD138 expression in normal myeloid, acute lymphoblastic and myeloblastic leukemia cells," Acta Histochem, 2003, 105, pp. 213-221.
Seftalioglu et al., "Syndecan-1 (CD138) expression in acute myeloblastic leukemia cells—an immuno electron microscopic study," Acta Oncol, 2003, 42, pp. 71-74.
Senter et al., "Cures and regressions of established tumors with monoclonal antibody auristatin conjugates," Abstract # 2062, Proc. Am. Assoc. Can. Res. (San Francisco, CA: American Association for Cancer Res.), Mar. 2002, 43 pp. 414-415.
Sievers et al., "Efficacy and safety of gemtuzumab ozogamicin in patients with CD33-positive acute myeloid leukemia in first relapse," J. Clin. Oncol, 2001, 19, pp. 3244-3254.
Sievers et al., "Mylotarg: antibody-targeted chemotherapy comes of age," Curr. Opin. Oncol., 2001, 13, pp. 522-527.
Smith R., Single chain antibody variable region fragments; www.stanford.edu/~smithr/science/scfv.html (last updated in May 2001).
Stanley et al., "Syndecan-1 expression is induced in the stroma of infiltrating breast carcinoma," Am J Clin Pathol., Sep. 1999, 112(3), pp. 377-383.
Studnicka et al. "Human-engineered monoclonal antibodies retain full specific binding activity by preserving non-CDR complementarity-modulating residues," Protein Eng., 1994, 7(6), pp. 805-814.
Sun et al., "Large scale and clinical grade purification of syndecan-1+ malignant plasma cells," J Immunol Methods, Jun. 23, 1997, 205(1), pp. 73-79.
Tolcher et al., "Cantuzumab mertansine, a maytansinoid immunoconjugate directed to the CanAg antigen: a phase I, pharmacokinetic, and biologic correlative study," J Clin Oncol, 2003, 21, pp. 211-222.
Urashima et al., "The development of a model for the homing of multiple myeloma cells to human bone marrow," Blood, 1997, 90, pp. 754-765.
Vogel, CW, "Preparation of immunoconjugates using antibody oligosaccharide moieties. Methods in Molecular Biology: Bioconjugation protocols strategies and methods," 2004, 283, pp. 87-108.
Vooijs et al., "Efficacy and toxicity of plasma-cell-reactive monoclonal antibodies B-B2 and B-B4 and their immunotoxins," Cancer Immunol Immunother, 1996, 42, pp. 319-328.

(56) References Cited

OTHER PUBLICATIONS

Ward et al. "Binding activities of a repertoire of single immunoglobin variable domains secreted from *Escherichia coli*," Nature, 1989, 341, pp. 544-546.

Wargalla et al., "Rate of internalization of an immunotoxin correlates with cytotoxic activity against human tumor cells," Proc. Natl. Acad. Sci. USA, 1989, 86, pp. 5146-5150.

Wijdenes et al. "A plasmocyte selective monoclonal antibody (B-B4) recognizes syndecan-1," Br J Haematol, 1996, 94, pp. 318-323.

Wijdenes et al., "CD138" J Biol Regul Homeost Agents, Apr.-Jun. 2002, 16(2), pp. 152-155.

Wiksten et al. "Epithelial and stromal syndecan-1 expression as predictor of outcome in patients with gastric cancer," Int J Cancer, Jan. 20, 2001, 95(1), pp. 1-6.

Witzig et al., "Detection of myeloma cells in the peripheral blood by flow cytometry," Cytometry, 1996, 26, pp. 113-120.

Xie et al., "Pharmacokinetics and biodistribution of the antitumor immunoconjugate, cantuzumab mertansine (huC242-DM1), and its two components in mice," J Pharmacol Exp Ther, Mar. 2004, 308(3), pp. 1073-1082.

Yang et al., "Genetically fluorescent melanoma bone and organ metastasis models," Clin Cancer Res, 1999, 5, pp. 3549-3559.

Yang et al., "Whole-body optical imaging of green fluorescent protein-expressing tumors and metastases," Proc Natl Acad Sci U S A, 2000, 97, pp. 1206-1211.

Tassone et al., Proc Amer Assoc Cancer Res, vol. 45, abstract# 1425, Mar. 2004, abstract.

Supiot et al., "Compariosn of the Biologic Effects of MA5 and B-B4 Monoclonal Antibody Labeled with Iodine-131 and Bismuth-213 on Multiple Myeloma," Cancer, vol. 94, No. S4, pp. 1202-1209, 2002.

Tassone et al., "Cytotoxic activity of the maytansinoid immunoconjugate B-B4-DM1 against CD138+ multiple myeloma cells," Blood Journal, vol. 104 (12), Dec. 1, 2004, pp. 3688-3696.

Tassone et al., "In vitro and in vivo activity of the maytansinoid immunoconjugate huN901-N2'-Deacetyl-N2'-(3-Mercapto-1-Oxopropyl)-Maytansine against CD56+ Multiple Myeloma Cells," Cancer Research, vol. 64, Jul. 1, 2004, pp. 4629-4636.

Tassone et al, Blood, Nov. 16, 2003, vol. 102, 45th ASH meeting abstract 449s-450a (abstract).

Sharkey Robert M et al: "Targeted therapy of Cancer: new prospects for antibodies and immunoconjugates." in CA: A Cancer Journal for Clinicians Jul.-Aug. 2006, vol. 56, No. 4, pp. 226-243.

Turner et al.: "131I-Anti CD20 radioimmunotherapy of relapsed or refractory non-Hodgkins lymphoma: a phase II clim'cal trial of a nonmyeloablative dose regimen of chimeric rituximab radiolabeled in a hospital," in Cancer Biotherapy & Radiopharmaceuticals Aug. 2003, vol. 18, No. 4, pp. 513-524.

Israel et al.: "Plasmapheresis and inmunological control of cancer," in Lancet Sep. 18, 1976, vol. 2, No. 7986, pp. 642-643.

Cortesini: "Pancreas cancer and the role of soluble immunoglobulin-like transcript 3 (ILT3)," in JOP: Journal of the Pancreas 2007, vol. 8, No. 6, Nov. 1, 2007, pp. 697-703.

Tassone et al.: "Cytotoxic activity of the maytansinoid immunoconjugate B-B4-DM1 against CD138+ multiple myeloma cells," in Blood Dec. 1, 2004, vol. 104, No. 12, pp. 3688-3696.

Prinssen et al., "Biodistribution of 111 In-labelled engineered human antibody CTM01 (hCTM01) in ovarian cancer patients: influence of prior administration of unlabelled hCTM01." Cancer Immunology Immunotherapy, 1998, vol. 47, No. 1, pp. 39-46.

Beatty et al., "Effect of Specific Antibody Pretreatment on Liver Uptake of 111 In-labeled Anticarcinoembryonic Anitgen Monoclonal Antibody in Nude Mice Bearing Human Colon Cancer Xenografts," Cancer Research, 1989, vol. 49, No. 6, pp. 1587-1594.

Malsmar et al., "Soluble CD138: A new important marker in diagnosis of multiple myeloma", International Journal of Hematology. Supplement, 2002, vol. 76, No. Suppl.1, page 106, P292.

Seldel et al., "Serum syndecan-1: a new independent prognostic marker in multiple myeloma", Blood, 2000, vol. 95, No. 2. pp. 388-392.

Janasi et al., "Soluble syndecan-1 levels in different plasma cell dyscrasias and in different stages of multiple myeloma", Haematologica, 2004, vol. 89, No. 3, pp. 370-371.

\* cited by examiner

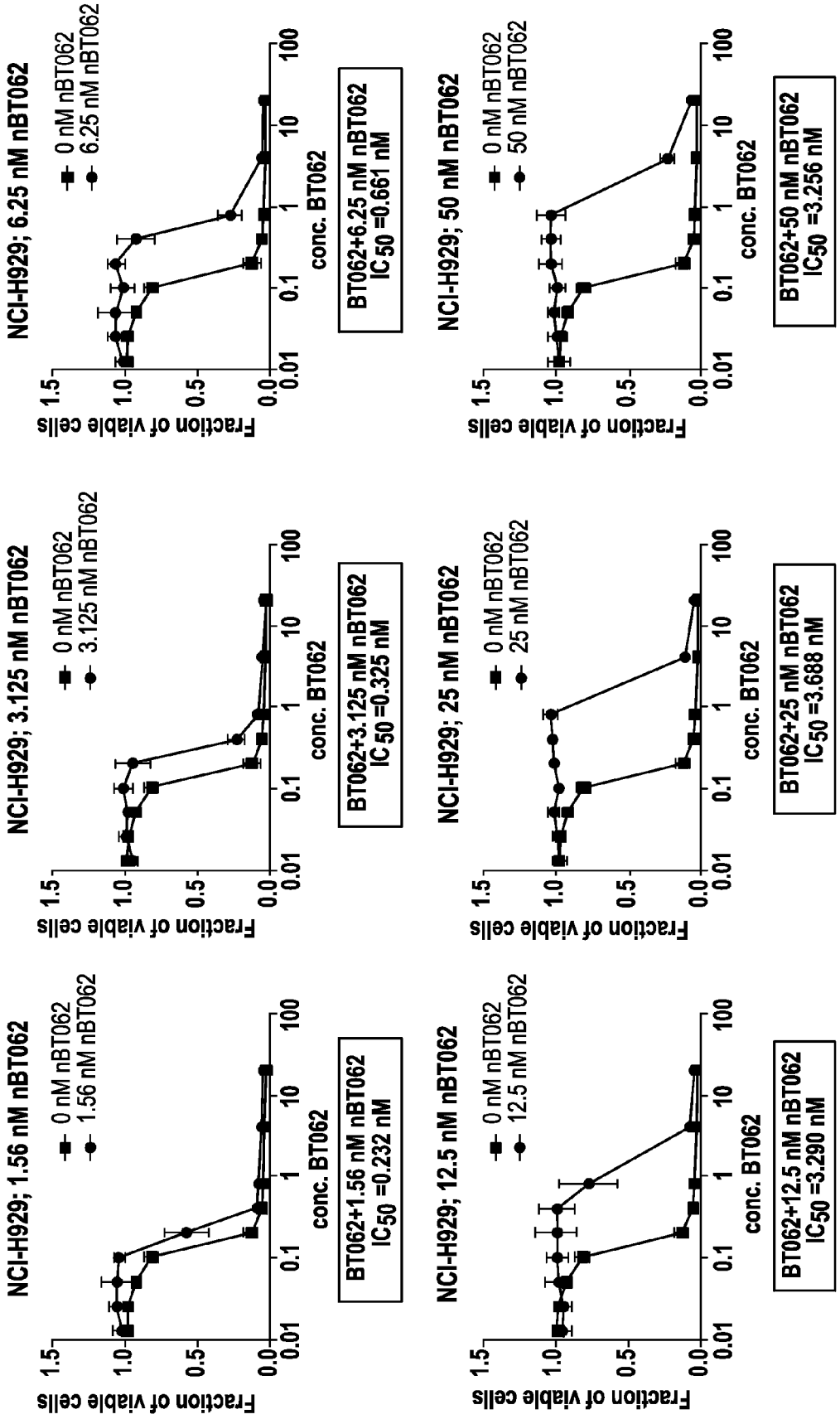

METHOD OF DECREASING CYTOTOXIC SIDE-EFFECTS AND IMPROVING EFFICACY OF IMMUNOCONJUGATES

CROSS REFERENCE TO RELATED APPLICATIONS

This application claims the benefit of U.S. provisional application 61/016,613, filed Dec. 26, 2007, and U.S. provisional application 61/016,630, filed Dec. 26, 2007, both of which are incorporated herein by reference in their entirety.

FIELD OF THE INVENTION

The present invention relates to methods and compositions that improve the targeting of immunoconjugates, in particular immunoconjugates directed at antigens that are expressed on target as well as non-target cells.

BACKGROUND

Immunoconjugates are promising candidates for the treatment of different medical indications, in particular for the treatment of a wide variety of cancers. For example, Tassone et al. (2004) reports excellent cytotoxic activity of the maytansinoid immunoconjugate B-B4-DM1 against CD138 positive multiple myeloma cells (see also US Patent Publ. 20070183971).

The publications and other materials, including patents, used herein to illustrate the invention and, in particular, to provide additional details respecting the practice are incorporated by reference. For convenience, the publications are referenced in the following text by author and date and are listed alphabetically by author in the appended bibliography.

A substantial body of research has concentrated on the development of systems in which an effector agent can be selectively delivered to a desired location or cell population, i.e., systems for a more targeted treatment of ailments with fewer toxic side effects. In spite of considerable progress that has been made, many of those delivery systems for the treatment of various diseases, for example, the treatment of cancer, are still ineffective and/or subject the patient to considerable risk.

Immunoconjugates comprise at least one targeting agent attached to at least one effector molecule. Such immunoconjugates can be categorized according to their effector molecules into, for example, drug immunoconjugates, immunotoxin conjugate and radioimmunoconjugates (Payne, 2003).

Efficiency in killing target cells is one key factor in the usefulness of an immunoconjugate. Efficiency can be influenced by the potency of the effector molecule (Blättler and Chari, 2001), by the ability of the effector to retain its potency (Chari et al., 1995; Liu et al., 1996; Ojima et al., 2002; Senter et al., 2002 and Sievers and Linenberger, 2001), by the tumor accessibility (Charter, 2001), by the level of expression of the target antigen on the target cell, by targeting agent affinity, and by the ability of the target cell to internalize the immunoconjugate (Wargalla, 1989).

One approach towards better efficiency involves the radioimmunoconjugate Zevalin. Y-90 Zevalin (Yttrium-90-labeled Ibritumomab-Tiuxetan) and In-111 Zevalin (Indium-111-labeled Ibritumomab-Tiuxetan) are radioimmunconjugates (Biogen-IDEC) based on Ibritumomab, the murine counterpart of Rituximab, conjugated with the chelator Tiuxetan, that has affinity for In-111 and Y-90. Both Ibritumomab (murine) and Rituximab (human), bind to CD20 which is widely expressed on B cells. CD20 does not internalize, modulate or shed and most likely plays a role in the $Ca^{2+}$ in- and efflux of cells. Rituximab when administered by itself (without Zevalin) is highly cytotoxic and results in the elimination of B cells (including cancerous B cells) and thus has become part of the standard treatment of aggressive lymphomas. The eliminated B cells are replaced by healthy B cells from lymphoid stem cells.

The Zevalin therapeutic regime involves both the unconjugated antibody Rituximab and the immunoconjugate Zevalin. Generally, a single infusion of Rituximab precedes a fixed dose of In-111 Zevalin administered as a 10 minutes IV push. This step is, after seven to nine days, followed by a second step that involves a second infusion of Rituximab prior to administration of Y-90 Zevalin as a 10 minutes IV push. The pre-treatment with Rituximab removes the bulk of B cells, while the remaining cells, which may include tumor cells resistant to treatment with Rituximab, can then be targeted with Zevalin. In-111/Y-90 Zevalin is generally not employed by itself due to side effects that would result from the B cell mediated distribution of the radioactivity throughout the patient's body.

This Zevalin treatment, which is indicated for patients with relapsed or refractory low-grade, follicular, or transformed B-cell non-Hodgkin's lymphoma, including patients with Rituximab refractory follicular non-Hodgkin's lymphoma, showed higher response rates in clinical trials compared to only Rituximab. It also showed promising results for patients who no longer responded to Rituximab.

Ideally an immunoconjugate specifically binds to the target cell population, such as a particular class of tumor cells, and hardly or not at all to any other cell, in particular not to cells that perform vital functions in the host organism. While some antigens well correlate to certain disease profiles, in the majority of cases the antigens are also expressed on cells that are not associated with the disease, that is, non-target cells. Depending on the importance of these healthy cells for the organism, the success of an immunoconjugate will to a large extent depend on how far these cells are affected by the treatment.

Thus, there remains a need for reducing the potential of side effects of immunoconjugates resulting from their interaction with non-targets that express the relevant antigen of the target cells. These include, in particular, cytotoxicity towards non-target cells as well as the overall reduction in efficiency of the immunoconjugate due to association with target molecules that have dissociated from the target cells. The reduction of cytotoxicity towards non-target cells is particularly important when the non-target cells play a vital role in the host system.

SUMMARY OF THE INVENTION

The present invention is directed at a method for improving targeting of immunoconjugates targeting cell bound antigen expressed on target cells comprising:
(a) providing a medium comprising said antigen, wherein said antigen is cell bound on target cells, non-target cells and/or is present in soluble form;
(b) sequestering cell bound antigen, soluble antigen and/or antigen expressing cells,
(c) administering an immunoconjugate targeting cell bound antigen expressed on target cells comprising a targeting agent for said antigen that is functionally attached to an effector molecule, wherein said sequestering in (b) improves the target cell targeting of said immunoconjugate. Preferably, the antigen internalizes into cells to which it is bound and/or is subject to shedding. The non-target cells may comprise cells such as epithelial cells, liver cells or any other cells that are not readily regenerated.

In particular, the present invention is directed at a method for improving tumor targeting of immunoconjugates targeting CD138 comprising:
(a) providing a medium comprising cell bound CD138 and/or soluble CD138;
(b) sequestering cell bound CD138, soluble CD138 and/or CD138 expressing cells,
(c) administering an immunoconjugate targeting cell bound CD138 comprising a targeting agent for CD138 that is functionally attached to an effector molecule, wherein said sequestering in (b) improves the tumor targeting of said immunoconjugate.

The present invention is also directed at pharmaceutical compositions and kits comprising an immunoconjugate targeting cell bound antigen (e.g., CD138) expressed on target cells (e.g., tumor cells) comprising a targeting agent for said antigen that is functionally attached to an effector molecule, and an unconjugated targeting agent.

The present invention provides a use of an immunoconjugate targeting cell bound CD138 comprising a targeting agent for CD138 that is functionally attached to an effector molecule for the manufacture of a medicament for the treatment of a tumor, wherein the medicament is to be administered to a patient in which cell bound CD138, soluble CD138 and/or CD138 expressing cells have been sequestered.

The present invention further provides a use of an immunoconjugate targeting cell bound CD138 comprising a targeting agent for CD138 that is functionally attached to an effector molecule for the manufacture of a medicament for the treatment of a tumor, wherein the medicament is to be administered as part of a treatment regime comprising the steps of:
(a) providing a medium comprising cell bound CD138 and/or soluble CD138;
(b) sequestering cell bound CD138, soluble CD138 and/or CD138 expressing cells, and
(c) administering the immunoconjugate.

In addition, the present invention provides an immunoconjugate targeting cell bound CD138 comprising a targeting agent for CD138 that is functionally attached to an effector molecule for use in the treatment of a tumor, wherein the immunoconjugate is to be administered to a patient in which cell bound CD138, soluble CD138 and/or CD138 expressing cells have been sequestered.

Further the present invention provides a use of an immunoconjugate targeting cell bound CD138 and an unconjugated CD138 targeting agent for the manufacture of a combined preparation for simultaneous, separate or sequential use in the treatment of a tumor, wherein the immunoconjugate comprises a targeting agent for CD138 that is functionally attached to an effector molecule and wherein the unconjugated CD138 targeting agent is capable of sequestering cell bound CD138, soluble CD138 and/or CD138 expressing cells.

Also, the present invention provides a medicament comprising an immunoconjugate targeting cell bound CD138 and an unconjugated CD138 targeting agent as a combined preparation for simultaneous, separate or sequential use in the treatment of a tumor, wherein the immunoconjugate comprises a targeting agent for CD138 that is functionally attached to an effector molecule and wherein the unconjugated CD138 targeting agent is capable of sequestering cell bound CD138, soluble CD138 and/or CD138 expressing cells.

In particular, in the above uses the sequestering of cell bound CD138, soluble CD138 and/or CD138 expressing cells improves the tumor targeting of the immunoconjugate.

The present invention also provides a use of an immunoconjugate targeting cell bound antigen expressed on target cells comprising a targeting agent for said antigen that is functionally attached to an effector molecule for the manufacture of a medicament for treating a patient, wherein the medicament is to be administered to a patient in which cell bound antigen, soluble antigen and/or antigen expressing cells have been sequestered.

The present invention further provides a use of an immunoconjugate targeting cell bound antigen expressed on target cells comprising a targeting agent for said antigen that is functionally attached to an effector molecule for the manufacture of a medicament for treating an individual, wherein the medicament is to be administered as part of a treatment regime comprising the steps of:
(a) providing a medium comprising said antigen, wherein said antigen is cell bound on target cells, non-target cells and/or is present in soluble form;
(b) sequestering cell bound antigen, soluble antigen and/or antigen expressing cells; and
(c) administering the immunoconjugate.

The present invention also provides an immunoconjugate targeting cell bound antigen expressed on target cells comprising a targeting agent for said antigen that is functionally attached to an effector molecule for use in the treatment of an individual, wherein the immunoconjugate is to be administered to a patient in which cell bound antigen, soluble antigen and/or antigen expressing cells have been sequestered.

Further, the present invention provides a use of an immunoconjugate targeting cell bound antigen expressed on target cells and an unconjugated targeting agent for the manufacture of a combined preparation for simultaneous, separate or sequential use in the treatment of an individual, wherein the immunoconjugate comprises a targeting agent for the antigen that is functionally attached to an effector molecule and wherein the unconjugated targeting agent is capable of sequestering cell bound antigen, soluble antigen and/or antigen expressing cells.

Also, the present invention provides a medicament comprising an immunoconjugate targeting cell bound antigen expressed on target cells and an unconjugated targeting agent as a combined preparation for simultaneous, separate or sequential use in the treatment of an individual, wherein the immunoconjugate comprises a targeting agent for said antigen that is functionally attached to an effector molecule and wherein the unconjugated targeting agent is capable of sequestering cell bound antigen, soluble antigen and/or antigen expressing cells.

In one embodiment of the invention, the sequestering of cell bound antigen, soluble antigen and/or antigen expressing cells in the above uses improves the target cell targeting of said immunoconjugate.

In particular, the present invention can be applied to the treatment or prevention of a disease in an individual wherein the disease is one in which the target antigen expressed on the target cells is also present in soluble form and/or on non-target healthy cells and/or tissue. In one embodiment of the invention the target cell is a pre-cancerous or cancer cell.

DETAILED DESCRIPTION OF VARIOUS AND PREFERRED EMBODIMENTS OF THE INVENTION

Figure 1A:
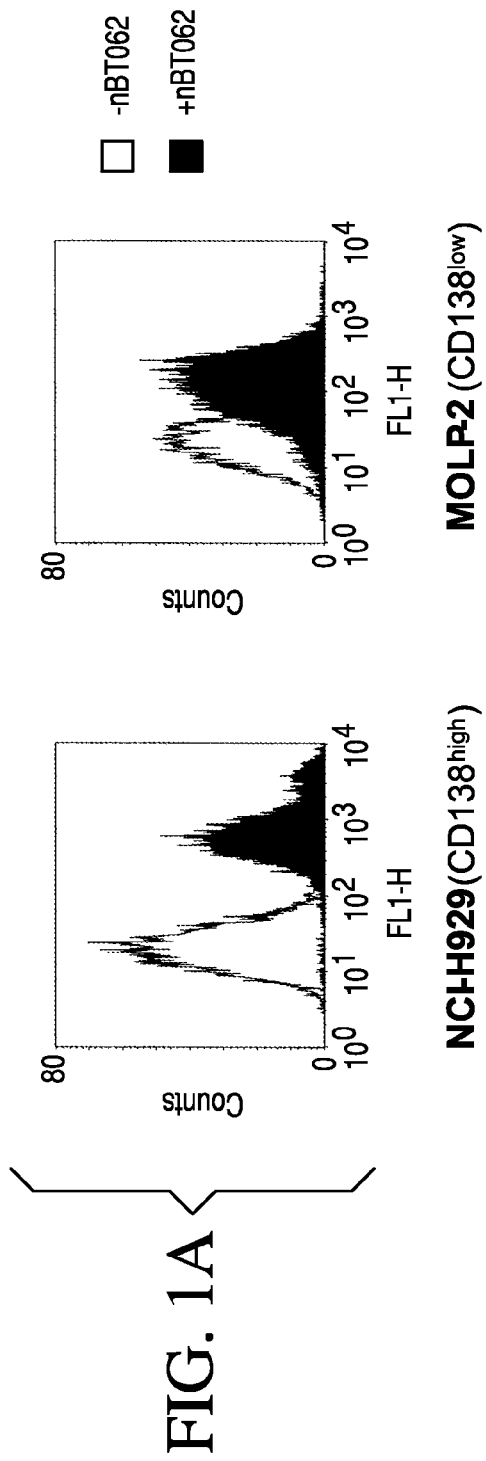
FIG. 1 shows in (A) CD138 expression on the surface of NCI-H929 and MOLP-2 (right) determined by FACS analysis. Bound nBT062 antibody as detected using a FITC-conjugated secondary antibody is shown in black. In the representative histogram plots, cell counts are plotted against fluorescence intensity measured in the FITC channel (FL1-H). Cells treated with the secondary antibody only served as controls (white). (B) shows the sensitivity of NCI-H929 and MOLP-2 cells against nBT062-SPDB-DM4 (conjugate) and against free toxin lacking the antibody moiety as measured in cell viability assays. Corresponding $IC_{50}$ values are given. The relative expression of CD138 on the cell surface was determined by FACS analysis and relative fluorescence intensities (RFI) are given. In addition, absolute receptor numbers per cell are shown as quantified by using the QIFIKIT. In (C) the Figure shows the sensitivity of MOLP-2 and NCI-H929 cells towards nBT062.

The present invention relates to a method of improving targeting, in particular tumor targeting, of immunoconjugates, in particular immunoconjugates having cell bound antigens as targets that are also expressed on non-target cells. The method comprises sequestering the antigen (e.g., CD138) which may be cell bound or soluble, via unconjugated targeting agent(s). In certain embodiments, the method also comprises sequestering cells expressing cell bound antigen. The sequestration preferably "shields" non-target cells from destruction by the immunoconjugate and/or reduces immunoconjugate binding to soluble antigen and/or antigen expressed on non-target cells. Thus, side effects resulting from immunoconjugate treatment are reduced and/or the efficiency of binding is improved allowing administration of a lower dosage of immunoconjugate and/or a higher dosage of immunoconjugate with a respectively lower occurrence of side effects.

In one embodiment, the unconjugated targeting agent according to the present invention is administered to cells of a subject in need of therapeutic treatment. The unconjugated targeting agent binds an antigen (e.g., CD138) which may or may not be cell bound. An immunoconjugate is administered subsequently or concurrently (e.g., in a single dosage or as part of a kit). Alternatively or additionally, e.g., the blood of the patient is first treated (pretreated) to sequester soluble, cell bound antigen and/or antigen expressing cells. Compared to the direct administration of the immunoconjugate (i.e., without the pretreatment with the unconjugated targeting agent) the viability of accessible non-target cells upon treatment with the immunoconjugate is improved by about 5%, about 10%, about 20%, about 30%, about 40%, about 50%, about 60% or even more.

In one example, the unconjugated targeting agent is nBT062 (DSM ACC287), which is administered to a patient with cancer as a single dose. In this example, an effective amount of nBT062 is administered intravenously so that the unconjugated targeting agent reaches soluble CD138 (CD138) and readily accessible cell bound CD138 promptly. Within four hours, the immunoconjugate BT062, which is described in more detail herein, is administered in an effective amount intravenously to the same patient. The immunoconjugate is internalized and the effector molecule(s) is/are released from the antibody target by natural means. The administration procedure may be repeated on the same patient after 5 to 10 days. The effective ratio of nBT062: BT062 employed is 10:1 and 3:1, respectively.

In a second example, nBT062 and BT062 are administered simultaneously as part of a pharmaceutical composition to a patient in need of tumor treatment. The target cells are CD138 expressing tumor cells. Both, nBT062 and BT062, are each administered in an effective amount. The dosage of the individual components of the composition and the effective ratio of nBT062 to BT062 is determined in cell culture prior to administration to allow an improvement of tumor targeting of the immunoconjugate. In particular, the viability of tumor target cells is, compared to the direct administration of the immunoconjugate, only slightly reduced by 1%, while the viability of the accessible non-target cells, also compared to the direct administration of the immunoconjugate, is doubled from 40% to 80%. When an effective amount of the immunoconjugate has bound the target cell, the immunoconjugate is internalized and the effector molecule or molecules are released from the antibody target by natural means.

In a third example, the alpha blocker prozosin is administered orally to a patient in need of tumor treatment prior to or concurrent with nBT062. Prozosin stimulates the peripheral circulation in the patient thus allowing nBT062 to more efficiently reach its destination, which, in the case of the unconjugated targeting agent, is a non-target cell, e.g., cells of the epithelium. The next day, BT062 is administered to said patient in an effective amount. An improvement of tumor targeting of the immunoconjugate is obtained. An effective ratio of 1:1 nBT062/BT062 is employed. When an effective amount of the immunoconjugate has bound the target cell, the immunoconjugate is internalized and the effector molecule or molecules are released from the antibody target by natural means.

In a fourth example, blood of a patient is run through a column in which nBT062 has been immobilized on sepharose beads that are packed into the column. sCD138 ("soluble"/"shielded" CD138) binds to the immobilized nBT062. The treatment is performed continuously for 2 hours. The so depleted blood is reintroduced into the patient, and sCD138 is washed off the column with a saline solution to prepare the column for the next procedure. Within 24 hours, the patient is treated with an effective amount of BT062.

In a fifth example, the patient's blood is pretreated as in the third example, but the patient is treated with a combination of antitrombin-3 and BT062, which are administered, each in an effective amount and at an effective ratio, intravenously.

In a sixth example, the patient's blood is subjected to plasmapheresis for two hours. Blood cells obtained are resuspended in replacement donor plasma or saline with added proteins and are reintroduced into the patient. The immunoconjugate is then administered to the patient as in examples 3 or 4.

CD138 or sydecan-1 (also described as SYNDL; SYNDECAN; SDC; SCD1; CD138 ANTIGEN, SwissProt accession number: P18827 human) is an integral membrane glycoprotein that was originally described to be present on cells of epithelial origin, and subsequently found on hematopoietic cells (Sanderson, 1989). In malignant hematopoiesis, CD138 is highly expressed on the majority of multiple myeloma (MM) cells, ovarian carcinoma, kidney carcinoma, gall bladder carcinoma, breast carcinoma, prostate cancer, lung cancer, colon carcinoma cells and cells of Hodgkin's and non-Hodgkin's lymphomas, chronic lymphocytic leukemia (CLL) (Horvathova, 1995), acute lymphoblastic leukemia (ALL), acute myeloblastic leukemia (AML) (Seftalioglu, 2003 (a); Seftalioglu, 2003 (b)), gallbladder (GB) carcinoma (Roh et al, 2008), solid tissue sarcomas, colon carcinomas, as well as other hematologic malignancies and solid tumors that express CD138 (Carbone et al., 1999; Sebestyen et al., 1999; Han et al., 2004; Charnaux et al., 2004; O'Connell et al., 2004; Orosz and Kopper, 2001).

Other cancers that have been shown to be positive for CD138 expression are many ovarian adenocarcinomas, transitional cell bladder carcinomas, kidney clear cell carcinomas, squamous cell lung carcinomas; breast carcinomas and uterine cancers (see, for example, Davies et al., 2004; Barbareschi et al., 2003; Mennerich et al., 2004; Anttonen et al., 2001; Wijdenes, 2002).

In the normal human hematopoietic compartment, CD138 expression is restricted to plasma cells (Wijdenes, 1996; Chilosi, 1999) and is not expressed on peripheral blood lymphocytes, monocytes, granulocytes, and red blood cells. In particular, $CD34^+$ stem and progenitor cells do not express CD138 and anti-CD138 mAbs do not affect the number of colony forming units in hematopoietic stem cell cultures (Wijdenes, 1996). In non-hematopoietic compartments, CD138 is mainly expressed on simple and stratified epithelia within the lung, liver, skin, kidney and gut. Only a weak staining was seen on endothelial cells (Bernfield, 1992; Vooijs, 1996). It has been reported that CD138 exists in polymorphic forms in human lymphoma cells (Gattei, 1999).

Monoclonal antibodies B-B4, BC/B-B4, B-B2, DL-101, 1 D4, M115, 1.BB.210, 2Q1484, 5F7, 104-9, 281-2 in particular B-B4 have been reported to be specific to CD138. Of those B-B4, 1D4 and MI15 recognized both the intact molecule and the core protein of CD138 and were shown to recognize either the same or closely related epitopes (Gattei, 1999). Previous studies reported that B-B4 did not recognize soluble CD138, but only CD138 in membrane bound form (Wijdenes, 2002).

B-B4, a murine IgG1 mAb, binds to a linear epitope between residues 90-95 of the core protein on human syndecan-1 (CD138) (Wijdenes, 1996; Dore, 1998). Consistent with the expression pattern of CD138, B-B4 was shown to strongly react with plasma cell line RPM18226, but not to react with endothelial cells. Also consistent with the expression pattern of CD138, B-B4 also reacted with epithelial cells lines A431 (keratinocyte derived) and HepG2 (hepatocyte derived). An immunotoxin B-B4-saporin was also highly toxic towards the plasma cell line RPM18226, in fact considerably more toxic than free saporin. However, from the two epithelial cell lines tested, B-B4-saporin showed only toxicity towards cell line A431, although in a clonogenic assay B-B4 saporin showed no inhibitory effect on the outgrowth of A431 cells (Vooijs, 1996). Other researchers reported lack of specificity of MM-associated antigens against tumors (Couturier, 1999).

nBT062 is a CD138 specific chimeric human/murine antibody based on B-B4, which has the same binding specificity for CD138 as its parental antibody, B-B4 (B-B4 chimeric antibodies are generally also referred to herein as c-B-B4). Chinese hamster ovary cells expressing nBT062 have been deposited with the DSMZ-Deutsche Sammlung von Mikroorganismen und Zellkulturen GmbH, Mascheroder Weg 1, D-38124 Braunschweig on Dec. 11, 2007. The identification number is DSM ACC2875. BT062 is an immunoconjugate comprising the CD138-specific chimeric antibody nBT062 that is conjugated via a linker with a cytostatic maytansinoid derivative. Immunoconjugates comprising nBT062 and a maytansinoid effector molecule are often characterized in terms of their linker and maytansinoid effector, e.g., BT062-SMCC-DM1, is an immunoconjugate comprising nBT062, SMCC (a noncleavable linker containing a thioester bond) and DM1 as an effector. More generically, an immunoconjugate containing nBT062 and an effector molecule may also be described as nBT062-linker-effector or just as nBT062-effector (nBT062N, wherein N is any effector described herein).

A "targeting agent" according to the present invention is able to associate with a molecule expressed by a target cell and includes peptides and non-peptides. In particular, targeting agents according to the present invention include targeting antibodies and non-immunoglobulin targeting molecules, which may be based on non-immunoglobulin proteins, including, but not limited to, AFFILIN® molecules, ANTI-CALINS® and AFFIBODIES®. Non-immunoglobulin targeting molecules also include non-peptidic targeting molecules such as targeting DNA and RNA oligonucleotides (aptamers), but also physiological ligands, in particular ligands of the antigen in question, such as CD138.

A "targeting antibody" according to the present invention is or is based on a natural antibody or is produced synthetically or by genetic engineering and binds to an antigen on a cell or cells (target cell(s)) of interest. A targeting antibody according to the present invention includes a monoclonal antibody, a polyclonal antibody, a multispecific antibody (for example, a bispecific antibody), or an antibody fragment. The targeting antibody may be engineered to, for example, improve its affinity to the target cells (Ross, 2003) or diminish its immunogenicity. The targeting antibody may be attached to a liposomal formulation including effector molecules (Carter, 2003). An antibody fragment comprises a portion of an intact antibody, preferably the antigen binding or variable region of the intact antibody. Examples of antibody fragments according to the present invention include Fab, Fab', $F(ab')_2$, and Fv fragments, but also diabodies; domain antibodies (dAb) (Ward, 1989; U.S. Pat. No. 6,005,079); linear antibodies; single-chain antibody molecules; and multispecific antibodies formed from antibody fragments. In a single chain variable fragment antibody (scFv) the heavy and light chains (VH and VL) can be linked by a short amino acid linker having, for example, the sequence $(glycine_4 serine)_n$, which has sufficient flexibility to allow the two domains to assemble a functional antigen binding pocket. Addition of various signal sequences may allow for more precise targeting of the targeting antibody. Addition of the light chain constant region (CL) may allow dimerization via disulphide bonds, giving increased stability and avidity. Variable regions for constructing the scFv can, if a mAb against a target of interest is available, be obtained by RT-PCR which clones out the variable regions from mRNA extracted from the parent hybridoma. Alternatively, the scFv can be generated de novo by phage display technology (Smith, 2001). A bispecific antibody according to the present invention may, for example, have at least one arm that is reactive against a target tissue and one arm that is reactive against a linker moiety (United States Patent Publication 20020006379). A bispecific antibody according to the present invention may also bind to more than one antigen on a target cell (Carter, 2003). An antibody according to the present invention may be modified by, for example, introducing cystein residues to introduce thiol groups (Olafsen, 2004).

In accordance with the present invention, the targeting antibody may be derived from any source and may be, but is not limited to, a camel antibody, a murine antibody, a chimeric human/mouse antibody such as nBT062 or a chimeric human/monkey antibody, in particular, a chimeric human/monkey antibody with the monkey portion stemming from a cynomolgus monkey.

Humanized antibodies are antibodies that contain sequences derived from a human-antibody and from a non-human antibody and are also within the scope of the present invention. Suitable methods for humanizing antibodies include CDR-grafting (complementarity determining region grafting) (EP 0 239 400; WO 91/09967; U.S. Pat. Nos. 5,530, 101; and 5,585,089), veneering or resurfacing (EP 0 592 106; EP 0 519 596; Padlan, 199; Studnicka et al., 1994; Roguska et al., 1994), chain shuffling (U.S. Pat. No. 5,565,332) and Delmmunosation™ (Biovation, LTD). In CDR-grafting, the mouse complementarity-determining regions (CDRs) from, for example, mAb B-B4 are grafted into human variable frameworks, which are then joined to human constant regions, to create a human B-B4 antibody. Several antibodies humanized by CDR-grafting are now in clinical use, including MYLOTARG (Sievers et al., 2001) and HECEPTIN (Pegram et al, 1998).

The resurfacing technology uses a combination of molecular modeling, statistical analysis and mutagenesis to alter the non-CDR surfaces of antibody variable regions to resemble the surfaces of known antibodies of the target host. Strategies and methods for the resurfacing of antibodies, and other methods for reducing immunogenicity of antibodies within a different host, are disclosed, for example, in U.S. Pat. No. 5,639,641. Human antibodies can be made by a variety of methods known in the art including phage display methods. See also U.S. Pat. Nos. 4,444,887, 4,716,111, 5,545,806, and 5,814,318; and international patent application publications WO 98/46645, WO 98/50433, WO 98/24893, WO 98/16654, WO 96/34096, WO 96/33735, and WO 91/10741.

Fully human antibodies may also been used. Those antibodies can be selected by the phage display approach, where CD138 or an antigenic determinant thereof is used to selectively bind phage expressing, for example, B-B4 variable regions (see, Krebs, 2001). This approach is advantageously coupled with an affinity maturation technique to improve the affinity of the antibody.

In one embodiment, the targeting antibody is, in its unconjugated form, moderately or poorly internalized. Moderate internalization constitutes about 30% to about 75% internalization of antibody, poor internalization constitutes about 0.01% to up to about 30% internalization after 3 hours incubation at 37° C. In another preferred embodiment the targeting antibody binds to CD138, for example, antibodies B-B4, BC/B-B4, B-B2, DL-101, 1 D4, MI15, 1.BB.210, 2Q1484, 5F7, 104-9, 281-2 in particular B-B4 or nBT062. nBT062 is a chimerized B-B4 antibody. Hybridoma cells, which were generated by hybridizing SP02/0 myeloma cells with speen cells of Balb/c mice have been deposited with the DSMZ-Deutsche Sammlung von Mikroorganismen und Zellkulturen GmbH, Mascheroder Weg 1, D-38124 Braunschweig on Dec. 11, 2007. The identification number is DSM ACC2874. When, in the context of the present invention, the name of a specific antibody is combined with the term "targeting antibody" such as "nBT062 targeting antibody," this means that this targeting antibody has the binding specificity of the antibody nBT062. If a targeting antibody is said to be "derived from" a specified antibody, this means that this targeting antibody has the binding specificity of this antibody, but might take any form consistent with the above description of a targeting antibody.

"Non-immunoglobulin targeting molecules" according to the present invention include targeting molecules derived from non-immunoglobulin proteins as well as non-peptidic targeting molecules. Small non-immunoglobulin proteins which are included in this definition are designed to have specific affinities towards, in particular surface expressed CD138. These small non-immunoglobulin proteins include scaffold based engineered molecules such as Affilin® molecules that have a relatively low molecular weight such as between 10 kDa and 20 kDa. Appropriate scaffolds include, for example, gamma crystalline. Those molecules have, in their natural state, no specific binding activity towards the target molecules. By engineering the protein surfaces through locally defined randomization of solvent exposed amino acids, completely new binding sites are created. Former non-binding proteins are thereby transformed into specific binding proteins. Such molecules can be specifically designed to bind a target, such as CD138, and allow for specific delivery of one or more effector molecules (see, scil Proteins GmbH, 2004). Another kind of non-immunoglobulin targeting molecules are derived from lipocalins, and include, for example ANTICALINS®, which resemble in structure somewhat immunoglobulins. However, lipocalins are composed of a single polypeptide chain with 160 to 180 amino acid residues. The binding pocket of lipocalins can be reshaped to recognize a molecule of interest with high affinity and specificity (see, for example, Beste et al., 1999). Artificial bacterial receptors such as those marketed under the trademark Affibody® (Affibody AB) are also within the scope of the present invention. These artificial bacterial receptor molecules are small, simple proteins and may be composed of a three-helix bundle based on the scaffold of one of the IgG-binding domains of Protein A (Staylococcus aureus). These molecules have binding properties similar to many immunoglobulins, but are substantially smaller, having a molecular weight often not exceeding 10kDa and are also comparatively stable. Suitable artificial bacterial receptor molecules are, for example, described in U.S. Pat. Nos. 5,831,012; 6,534,628 and 6,740,734.

Other "non-immunoglobulin targeting molecules" are physiological ligands of the antigen in question. Physiological ligands of CD138 include for example, but not limited to, ADAMTS4 (aggrecanase-1), antithrombin-3, bFGF, cathepsin G, CCL5 (RANTES), CCL7, CCL11, CCL17, CD44, collagens (collagen type 1, collagen type 2, collagen type 3, collagen type 4, collagen type 5, collagen type 6), CXCL1, elastase, gp120, HGF [hepatocyte growth factor], laminin-1, laminin-2, laminin-5, midkine, MMP-7, neutrophil elastase, and pleiotrophin (HBNF, HBGF-8).

Non-peptidic targeting molecules include, but are not limited to, to DNA and RNA oligonucleotides that bind to CD138 (aptamers).

An "unconjugated targeting agent" as used herein, is in certain embodiments of the invention, a targeting agent that is not part of an immunoconjugate as defined herein, i.e. a targeting agent that is not attached to an effector molecule. However, in other embodiments and as will be detailed below, the "unconjugated targeting agent" is attached to a non-effector molecule, for example, to a matrix. In yet other embodiments, the unconjugated targeting agent may be attached to a dye molecule for monitoring. Unconjugated targeting agents according to the present invention preferably are not systemically cytotoxic for the cells they bind to that is, over time the unconjugated targeting agents do not induce cell death of populations of those cells.

The targeting agents of the present invention bind antigens expressed on target cells, in particular tumor cells, but also antigens expressed on non-target cells, though generally to different degrees. Non-target cells according to the present invention include cells expressing the target specific antigen, i.e., the antigen targeted by the immunoconjugate, such as CD138, but generally do so in considerably lower concentrations (such as a third, a fourth, a fifth or a sixth of the expression on the tumor cells) and do not have tumor cell/disease properties. Such non-target cells vary from antigen to antigen, but may include epithelial cells, liver cells or any other cells that are not readily regenerated.

An "effector molecule" according to the present invention is a molecule or a derivative, or an analogue thereof that is attached to a targeting agent and exerts a desired effect, for example apoptosis, or another type of cell death, or a continuous cell cycle arrest on the target cell or cells. Effector molecules according to the present invention include molecules that can exert desired effects in a target cell and include, but are not limited to, toxins, drugs, in particular low molecular weight cytotoxic drugs, radionuclides, biological response modifiers, pore-forming agents, ribonucleases, proteins of apoptotic signaling cascades with apoptosis-inducing activities, cytotoxic enzymes, prodrug activating enzymes, antisense oligonucleotides, antibodies or cytokines as well as functional derivatives or analogues/fragments thereof. Toxins may include bacterial toxins, such as, but not limited to, Diphtheria toxin or Exotoxin A, plant toxins, such as but not limited to, Ricin. Proteins of apoptotic signaling cascades with apoptosis-inducing activities, include, but are not limited to, Granzyme B, Granzyme A, Caspase-3, Caspase-7, Caspase-8, Caspase-9, truncated Bid (tBid), Bax and Bak.

In certain embodiments the effector has high non-selective toxicity, including systemic toxicity, when in its native form ("unconjugated effector"), that is, is non selective with regard to one or more target cells or types of target cells, in particular disease targets. The "native form" of an effector molecule of the present invention is an effector molecule before being attached to the targeting agent to form an immunoconjugate, that is, as it exists when not attached to the targeting agent. It can also be referred to as just the effector molecule or the unconjugated effector. In another preferred embodiment, the non-selective toxicity of the effector molecule is substantially eliminated upon conjugation to the targeting agent, that is, to the degree that any remaining non-selective toxicity is clinically acceptable. In another preferred embodiment, the effector molecule causes, upon reaching the target cell, death or continuous cell cycle arrest in the target cell. A drug-effector molecule according to the present invention includes, but is not limited to, a drug including, for example, small highly cytotoxic drugs that act as inhibitors of tubulin polymerization such as maytansinoids, dolastatins, auristatin and cryptophycin; DNA alkylating agents like CC-1065 analogues or derivatives (U.S. Pat. Nos. 5,475,092; 5,585,499; 6,716,821) and duocarmycin; enediyne antibiotics such as calicheamicin and esperamicin; and potent taxoid (taxane) drugs (Payne, 2003). Maytansinoids and calicheamicins are particularly preferred. An effector maytansinoid includes maytansinoids of any origin, including, but not limited to synthetic maytansinol and maytansinol analogue and derivative. Doxorubicin, daunomycin, methotrexate, vinblastine, neocarzinostatin, macromycin, trenimon and α-amanitin are some other effector molecules within the scope of the present invention. Also within the scope of the present invention are antisense DNA molecules as effector molecules. When the name of, for example, a specific drug or class of drugs is combined herein with the term "effector" or "effector molecule," reference is made to an effector of an immunoconjugate according to the present invention that is based on the specified drug or class of drugs.

Maytansine is a natural product originally derived from the Ethiopian shrub *Maytenus serrata* (Remillard, 1975; U.S. Pat. No. 3,896,111). This drug inhibits tubulin polymerization, resulting in mitotic block and cell death (Remillard, 1975; Bhattacharyya, 1977; Kupchan, 1978). The cytotoxicity of maytansine is 200-1000-fold higher than that of anticancer drugs in clinical use that affect tubulin polymerization, such as Vinca alkaloids or taxol. However, clinical trials of maytansine indicated that it lacked a therapeutic window due to its high systemic toxicity. Maytansine and maytansinoids are highly cytotoxic but their clinical use in cancer therapy has been greatly limited by their severe systemic side-effects primarily attributed to their poor selectivity for tumors. Clinical trials with maytansine showed serious adverse effects on the central nervous system and gastrointestinal system.

Maytansinoids have also been isolated from other plants including seed tissue of *Trewia nudiflora* (U.S. Pat. No. 4,418, 064)

Certain microbes also produce maytansinoids, such as maytansinol and C-3 maytansinol esters (U.S. Pat. No. 4,151, 042).

The present invention is directed to maytansinoids of any origin, including synthetic maytansinol and maytansinol analogues which are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,371,533; 4,424,219 and 4,151,042.

In a preferred embodiment, the maytansinoid is a thiol-containing maytansinoid and is more preferably produced according to the processes disclosed in U.S. Pat. No. 6,333, 410 to Chari et al or in Chari et al.(Chari, 1992).

DM-1 ($N^2$-deacetyl-$N^2$-(3-mercapto-1-oxopropyl)-maytansine) is a preferred effector molecule in the context of the present invention. DM1 is 3- to 10-fold more cytotoxic than maytansine, and has been converted into a pro-drug by linking it via disulfide bond(s) to a monoclonal antibody directed towards a tumor-associated antigen. Certain of these conjugates (sometimes called "tumor activated prodrugs" (TAPs)) are not cytotoxic in the blood compartment, since they are activated upon associating with a target cells and internalized, thereby releasing the drug (Blättler, 2001). Several antibody-DM1 conjugates have been developed (Payne, 2003), and been evaluated in clinical trials. For example, huC242-DM1 treatment in colorectal cancer patients was well tolerated, did not induce any detectable immune response, and had a long circulation time (Tolcher, 2003).

Other particularly preferred maytansinoids comprise a side chain that contains a sterically hindered thiol bond such as, but not limited to, maytansinoids $N^{2'}$-deacetyl-$N^{2'}$-(4-mercapto-1-oxopentyl)-maytansine, also referred to as "DM3," and $N^{2'}$-deacetyl-$N^{2'}$-(4-methyl-4-mercapto-1-oxopentyl)-maytansine, also referred to as "DM4."

DNA alkylating agents are also particularly preferred as effector molecules and include, but are not limited to, CC-1065 analogues or derivatives. CC-1065 is a potent antitumor-antibiotic isolated from cultures of *Streptomyces zelensis* and has been shown to be exceptionally cytotoxic in vitro (U.S. Pat. No. 4,169,888). Within the scope of the present invention are, for examples the CC-1065 analogues or derivatives described in U.S. Pat. Nos. 5,475,092, 5,585,499 and 5,739,350. As the person skilled in the art will readily appreciate, modified CC-1065 analogues or derivatives as described in U.S. Pat. No. 5,846,545 and prodrugs of CC-1065 analogues or derivatives as described, for example, in U.S. Pat. No. 6,756,397 are also within the scope of the present invention. In certain embodiments of the invention, CC-1065 analogues or derivatives may, for example, be synthesized as described in U.S. Pat. No. 6,534,660.

Another group of compounds that make preferred effector molecules are taxanes, especially highly potent ones and those that contain thiol or disulfide groups. Taxanes are mitotic spindle poisons that inhibit the depolymerization of tubulin, resulting in an increase in the rate of microtubule assembly and cell death. Taxanes that are within the scope of the present invention are, for example, disclosed in U.S. Pat. Nos. 6,436,931; 6,340,701; 6,706,708 and United States Patent Publications 20040087649; 20040024049 and 20030004210. Other taxanes are disclosed, for example, in U.S. Pat. No. 6,002,023, U.S. Pat. No. 5,998,656, U.S. Pat. No. 5,892,063, U.S. Pat. No. 5,763,477, U.S. Pat. No. 5,705,508, U.S. Pat. No. 5,703,247 and U.S. Pat. No. 5,367,086. As the person skilled in the art will appreciate, PEGylated taxanes such as the ones described in U.S. Pat. No. 6,596,757 are also within the scope of the present invention.

Calicheamicin effector molecules according to the present invention include gamma 11, N-acetyl calicheamicin and other derivatives of calicheamicin. Calicheamicin binds in a sequence-specific manner to the minor groove of DNA, undergoes rearrangement and exposes free radicals, leading to breakage of double-stranded DNA, resulting in cell apoptosis and death. One example of a calicheamicin effector molecule that can be used in the context of the present invention is described in U.S. Pat. No. 5,053,394.

Figure 5:
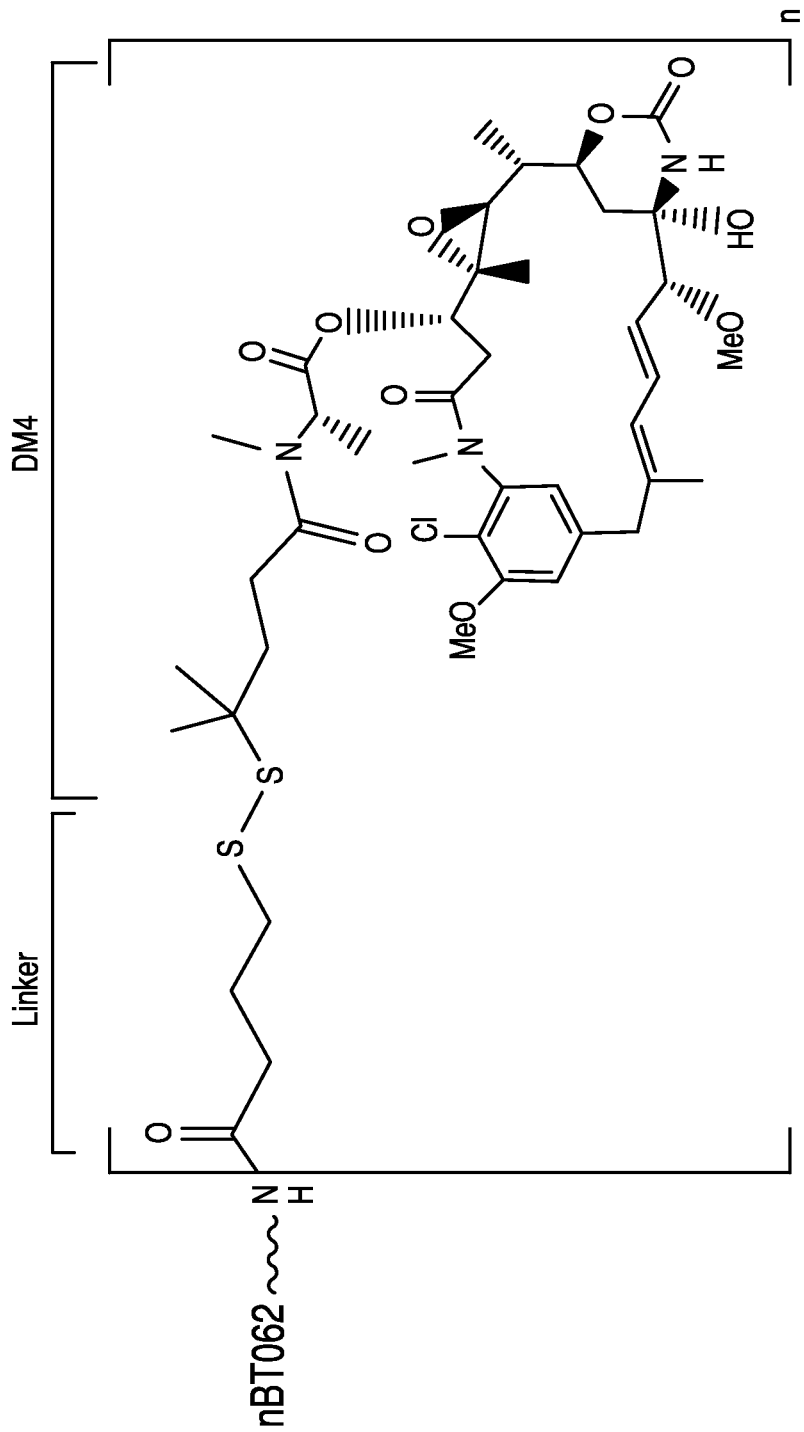
FIG. 5 shows a functional attachment of the effector to the antibody in the immunoconjugate BT062.

An "immunoconjugate" according to the present invention comprises at least one targeting agent, in particular a targeting antibody, and one or more effector molecules. The immunoconjugate might comprise further molecules for example for stabilization. For immunoconjugates, the term "conjugate" is generally used to define the operative association (i.e., functional attachment) of the targeting agent with one or more effector molecules and is not intended to refer solely to any type of operative association, and is particularly not limited to chemical "conjugation". So long as the targeting agent is able to bind to the target site and the attached effector functions sufficiently as intended, particularly when delivered to the target site, any mode of attachment will be suitable. The conjugation methods according to the present invention include, but are not limited to, direct attachment of the effector molecule to the targeting antibody, with or without prior modification of the effector molecule and/or the targeting antibody or attachment via linkers. Linkers can be categorized functionally into, for example, acid labile, photosensitive, enzyme cleavable linkers etc. Other suitable linkers may include disulfide bonds and non-cleavable bonds, such as, but not limited to Sulfosuccinimidyl maleimidomethyl cyclohexane carboxylate (SMCC), which is a heterobifunctional linker capable of linking compounds with SH-containing compounds. Bifunctional and heterobifunctional linker molecules, such as carbohydrate-directed heterobifunctional linker molecules, such as S-(2-thiopyridyl)-L-cysteine hydrazide (TPCH), are also within the scope of the present invention (Vogel, 2004). The effector molecule, such as a maytansinoid, may be conjugated to the targeting antibody via a two reaction step process, including as a first step modification of the targeting antibody with a cross-linking reagent such as N-succinimidyl pyridyldithiopropionate (SPDP) to introduce dithiopyridyl groups into the targeting antibody. In a second step, a reactive maytansinoid having a thiol group, such as DM1 or DM4, may be added to the modified antibody, resulting in the displacement of the thiopyridyl groups in the modified antibody, and the production of disulfide-linked cytotoxic maytansinoid/antibody conjugate (U.S. Pat. No. 5,208,020). However, one-step conjugation processes such as the one disclosed in United States Patent Publication 20030055226 to Chari et al are also within the scope of the present invention. In one embodiment of the present invention multiple effector molecules of the same or different kind are functionally attached to a targeting antibody. FIG. 5 shows an examplatory functional attachment as present in the immunoconjugate BT062 (nBT062-SPDP-DM4). As the Figure indicates on average, 3.5 DM4 molecules are attached to the antibody.

CC-1065 analogues or derivatives may be conjugated to the targeting agent via for example PEG linking groups as described in U.S. Pat. No. 6,716,821.

Calicheamicins may be conjugated to the targeting antibodies via linkers (U.S. Pat. No. 5,877,296 and U.S. Pat. No. 5,773,001) or according to the conjugation methods disclosed in U.S. Pat. No. 5,712,374 and U.S. Pat. No. 5,714,586. Another preferred method for preparing calicheamicin conjugates is disclosed in Unites States Patent Publication 20040082764. The immunoconjugates of the present invention also include recombinant fusion proteins.

The unconjugated targeting agents and/or immunoconjugates of the present invention can be provided in vivo and ex vivo. In many embodiments the treatment regime will include an in vivo as well as an ex vivo portion. For example, the blood of the patient may be first subjected to plasmapheresis and after reintroduction of at least the blood cells (e.g., in plasma expander) into the patient, the patient may be subjected to treatment with the immunoconjugate. Other ex vivo methods include treatment of cell supernatant. Depending on the particular treatment regime, different media may be contacted with the unconjugated targeting agent and/or immunoconjugate. These media include, but are not limited to, blood, plasma, tissue and bone marrow.

The unconjugated targeting agent preferably binds to antigen having different configurations, including antigen present in soluble form such as soluble (shed) CD138 (sCD138). Such sCD138 is produced, e.g., during a process referred to as shedding. Shedding can occur naturally, but may also be induced by certain drugs that are administered to, e.g., a MM patient.

The unconjugated targeting agent may also bind to cell bound antigen such as CD138. This cell bound antigen may be expressed on the surface of a non-target cell, which are also referred to herein as non-tumor cells when the target cells are tumor cells. The unconjugated targeting agent may bind to the antigen expressed on such a non-tumor cell/non-target cell to an extent that it shields the non-tumor cell/non-target cell to different degrees from destruction by the immunoconjugate that is administered concomitantly or subsequently, or in certain embodiments, prior to the administration of the unconjugated targeting agent.

The time intervals between a "pretreatment" with the unconjugated targeting agent and the administration of the immunoconjugate may differ and may be as short as about 20 mins., about 30 mins, but may also be about 1 hour, about 2 hours, about 3 hours, about 4 hrs, about 5 hrs, but generally do not exceed 24 hours.

When the unconjugated targeting agent is said to sequester cells expressing CD138 reference is made to sequestering whole cells expressing CD138. For example, an unconjugated targeting agent that is attached to a matrix may sequester such a cell from blood contacted with this matrix.

A vasodilatory agent, as used herein, is any agent with vasodilatory activity. Included are in particular, alpha 1 receptor antagonists, i.e., alpha blockers such as, but not limited to, prozosin, terazosin or doxazosin. However, any other agent with vasodilatory activity is included in this definition such as, but not limited to, sodium nitroprussid, calcium antagonists, nitrates or ACE inhibitors (inhibitors of Angiotensin-Converting Enzyme (ACE)).

These agents may be administered using different routes. However, oral administration is preferred. In the context of the present invention such vasodilatory agents may, preferably, be administered either before or with the unconjugated targeting agent. This administration is generally followed by an administration of a suitable immunoconjugate. In a preferred embodiment, the administration of the immunoconjugate is timed at least ten to twelve hours subsequent to the administration of the vasodilatory agent. However, the most appropriate timing will depend on the particular vasodilatory agent used and is well within the skill of the person of ordinary skill in the art. It is preferred that the administration of the immunoconjugate will be timed so that the vasodilatory effects of the agent have substantially subsided.

A method according to the present invention is said to "improve tumor targeting" of an immunoconjugate when the immunoconjugate employed according to this method binds, and preferably destroys, a higher percentile of tumor cells than when the immunoconjugate, under otherwise equivalent conditions (route of administration, concentration etc.) is used as the sole effective ingredient. Tumor cells according to the present invention include cancer cells as well as pre-cancerous cells which may or may not form solid tumors. Thus, any abnormally growing cell is part for this definition.

A method according to the present invention is said to improve targeting of target cells of an immunoconjugate if the target cells are associated with a disease or disease state, but are not necessarily tumor cells.

The improvement in targeting, in particular tumor targeting may be expressed as a percentile. For example, about 20% improved tumor targeting means that a given amount of immunoconjugate, when administered to a patient, binds, e.g., 20% more of the target tumor cells than when administered as the sole effective agent.

A method according to the present invention is also said to "improve targeting of target cells" or to "improve tumor targeting" of an immunoconjugate when non-target cells, e.g., CD138 expressing non-tumor cells are shielded from binding by the immunoconjugate, preferably to an extent that prevents or diminishes the destruction of said non-tumor (non-target) cells, preferably to a degree that is clinically acceptable, which may, depending on the non-tumor cell in question and the locus and route of administration, vary. Acceptable levels of destruction of non-target/non-tumor cells may vary widely and might be, in certain embodiments be as low as about 1% of the total population of a certain type of accessible non-tumor cells of a patient's body or non-tumor cell in a particular organ or up to about 2, 3, 4, 5, 6, 7, 8, 9, 10, 15 or 20%. In certain cases, in particular when the administration can be confined, e.g., to a particular organ, this percentile may be even higher. In this context, an effective amount of an immunoconjugate means an amount that results in destruction, preferably by apoptosis, of tumor cells that the immunoconjugate binds to. An effective amount of unconjugated targeting agent means an amount that "shields" or "masks", e.g., non-tumor cells expressing CD138, that is, an amount of unconjugated targeting agent that is sufficient to impede or block access of an effective amount of immunoconjugate to non-tumor cells so that destruction of the cells is prevented. By masking non-tumor cells toxicity of the immunoconjugate towards the total accessible non-tumor cells/non-target cells is limited to a degree acceptable, e.g. to a clinically acceptable degree. Certain concentrations of unconjugated targeting agent may result in decreasing the sensitivity of total accessible non-tumor cell/non-target cell population to an immunoconjugate, The decrease in sensitivity of the total accessible non-tumor cells/non-target cells may reflected by an increase in $IC_{50}$ values, and can be quantified by sequestration values:

Sequestration [%]=100×($IC_{50}$ treat/$IC_{50}$direct)−100

$IC_{50}$ treat [nM] ... $IC_{50}$ value for the immunoconjugate when cells are treated (pre- or concomitant) with the unconjugated targeting agent $IC_{50}$ direct [nM] ... $IC_{50}$ value for the immunoconjugate when cells are treated directly with the unconjugated targeting agent The $IC_{50}$ treat value might be above 2, above 3, above 4, above 5, above 6, above 7, above 8, above 9, above 10 times the $IC_{50}$ direct value, resulting in sequestration values of above 100%, above 200%, above 300%, above 400%, above 500%, above 600%, above 700%, above 800%, above 900% and above 1000%. However, in certain embodiments, lower sequestration values such as above 20% or above 50% might already be desirable.

$IC_{50}$ values and sequestration values for both accessible non-target cells (e.g., $CD138^{low}$) and accessible target cells (e.g., $CD138^{high}$) can be calculated and compared and relative sequestration values can be calculated:

Relative Sequestration=sequestration(accessible non-target cells)/sequestration(accessible target cells)

Values higher than 1 indicate that the shielding of, e.g., $CD138^{low}$ cells is higher than that of, e.g., $CD138^{high}$ cells for a given concentration of unconjugated targeting agent, e.g., nBT062.

In the context of the present invention relative sequestration values of equal to or more than 10, equal to or more than 20, equal to or more than 30, equal to or more than 40 or equal to or more than 50 are preferred.

When an unconjugated targeting agent is administered to shield the accessible non-target cells, in particular non-tumor cells, as explained elsewhere herein it will shield also target cells. In a preferred embodiment the effective amount of unconjugated targeting agent does not or only slightly decrease the sensitivity of tumor target cells, resulting in no or a relative slight increase in viable tumor cells. The effective amount of immunoconjugate administered preferably still allows the desired degree of destruction tumor cells.

In a preferred embodiment a ratio of unconjugated targeting agent to immunoconjugate is chosen so that the sensitivity of the total accessible non-target cells is decreased to clinically acceptable levels so that the percentile of viable accessible non-target cells compared to the same cell not treated with an unconjuated targeting agent is increased, e.g., more than 10%, 20%, 30%, 40%, 50%, 60%, up to 100%, while the sensitivity of the target, e.g., tumor cells is only decreased by preferably few percentile points, such as 1%, 2%, 3%, 4%, 5%, 6%, 7%, 8%, 9% or 10%, 15%, 20%, preferably 0 to 10%, even more preferably, 0 to 5%. The effective ratio of unconjugated targeting agent to immunoconjugate is thus a ratio that decreases the sensitivity of accessible total non-tumor/non-target cells (and thus increase the % of viable non-tumor cells) to a clinically acceptable level, while retaining the sensitivity of the tumor cells (and thus maintain or only slightly increase the % of viable tumor cells) at a clinically desirable level.

While the acceptability of non-target cell destruction and/or target cell survival and thus the ratios of unconjugated targeting agent to immunoconjugate might vary from patient to patient (depending, e.g., on the overall condition or disease state of the patient) and the form and locus of administration (intravenous vs. contained injection into, e.g., a particular organ), the following ratio of unconjugated targeting agent to immunoconjugate are in one embodiment of the present invention preferred: about 1:2 to about 10:1, more preferably about 1:1 to about 8:1, even more preferably about 1:1 to about 5:1 and in particular about 2:1, about 3:1, about 4:1. In one embodiment of the present invention, administration is started at high ratios of unconjugated targeting agent/immunoconjugate, which is successively reduced. For example, in a first treatment a ratio of about 20:1 is used allowing full protection of non-target cells and is subsequently lowered to about 10:1. If no adverse side effects are observed, the ratios are lowered to about 9:1, about 8:1, about 7:1, about 6:1, about 5:1, about 4:1, about 3:1, about 2:1 and/or about 1:1 and, in certain embodiments, about 1:2. In certain embodiments of the present invention, pretreatment with, e.g., a vasidolatory agent allows the reduction of the ratio to about 1:1, about 1:2, about 1:3, about 1:4 or about 1:5. The person skilled in the art, however, will be readily able to adjust the ratios as required for a particular situation and patient.

The improvement in tumor targeting of an immunoconjugate may alternatively or additionally result from sequestration by physical separation of, e.g., sCD138 or entire cells expressing CD138. The later of these methods is in particular of interest in the treatment of late stage cancers, such as multiple myelomas. As a result, the same amount of immunoconjuate administered will bind more tumor cells, since sCD138 or entire cells expressing CD138 are removed from, e.g. blood. This may allow a reduction of the dose of immunoconjugate to be administered to achieve the desired target cell destruction and thus reduce potential or actual side effects of the immunoconjugate.

Plasmapheresis is one way, even though not the only way, of achieving physical separation of, e.g., sCD138. It involves the removal, treatment, and return of (components of) blood plasma from the blood circulation. Plasma is then removed from the blood by a cell separator via discontinuous or continuous flow centrifugation or plasma filtration. As will be described in more detail below, the method may or may not be employed in conjunction with an unconjuated targeting agent. Preferably, during plasmapheresis a percentile of soluble antigen is removed, e.g., at least about 5%, at least about 10%, at least about 20%, at least about 30%, at least about 40%, at least about 50% or more are removed from the blood of a patient.

A targeting agent may be attached to a matrix. If a CD138 specific targeting agent is attached to a matrix, this targeting agent is referred to herein as a "CD138-specific adsorber." For example, to deplete sCD138 from a biological fluid, a targeting agent, such as nBT062, may be immobilized on a matrix. Such an immobilization could be based on covalent bounds such as a coupling to aldehyde activated beads or other surfaces by primary amines via "reductive amination", but also on non-covalent bounds such as by binding of nBT062 to protein A or protein G or by binding of, e.g., a biotinylated antibody to a streptavidin or avidin coated matrix. As the person skilled in the art will appreciate, typical matrixes include, but are not limited to, agarose or sepharose beads, polyesters or activated polyester surfaces.

The improved targeting, in particular tumor targeting of the method of the present invention can in certain embodiments at least in part be attributed to the relatively high level of expression of antigen, such as CD138, on target cells, in particular tumor cells as opposed to non-target/non-tumor cells and/or a faster processing/internalization of, e.g., CD138 by tumor cells as opposed to non-tumor cells. Tassone et al. (2004) reports a CD138 expression on the mRNA level of primary positive multiple myeloma (MM) cells that is 50 to 200 times higher than on plasma cells. A FACS analysis revealed an about six times higher CD138 amount on the surface of MM cells relative to plasma cells. However, as the person skilled in the art will appreciate, a number of methods may be employed to determine the relative expression of an antigen such as CD 138 on tumor cells relative to non-tumor cells, which include the methods described above, but also, e.g., a direct comparison of the protein levels or the QIFIKIT method further described below. Any increased level of expression (e.g., 2, 3, 4, 5, 6, 7, 8 or 9 fold when measured by FACS or the QIFIKIT method) that the person skilled in the art would understand to constitute a basis for differentiating between tumor and non-tumor cells is within the scope of the present invention. Thus, a specific dosage of, e.g., unconjugated targeting agent may bind to a relative higher percentile of CD138 expressed at non-tumor cells than CD138 expressed at tumor cells. By providing a certain dosage of unconjugated targeting agent, for example, on average, about 10%, about 20%, about 30%, about 40%, about 50%, about 60%, about 70%, about 80%, about 90% or even more of CD138 expressed on non-tumor cells is bound by the unconjugated targeting agent, while a lower percentile, such as about 5%, about 10%, about 20%, about 30%, about 40%, about 50%, about 60%, about 70%, about 80% or more of CD138 expressed on tumor cells is bound. As the person skilled in the art will appreciate, different percentile combinations are within the scope of the present invention. For example, at a certain dosage of unconjugated targeting agent, on average, about 50% of CD138 expressed on non-tumor cells is bound by the unconjugated targeting agent, while due to higher expression levels and/or reduced accessibility (see following discussion), on average, only about 30% of CD138 expressed on tumor cells is bound by said unconjugated targeting agent. The relative higher level of binding will effectively shield a significant amount of non-tumor cells (e.g., about 80%, about 70%, about 60%, about 50%, about 40%, about 30%, about 20% about 10% or about 5%) from destruction by an immunoconjugate, while a substantial portion, but preferably substantially all, tumor cells can still be, e.g., subject to apoptosis by the immunoconjugate.

Figure 1B:
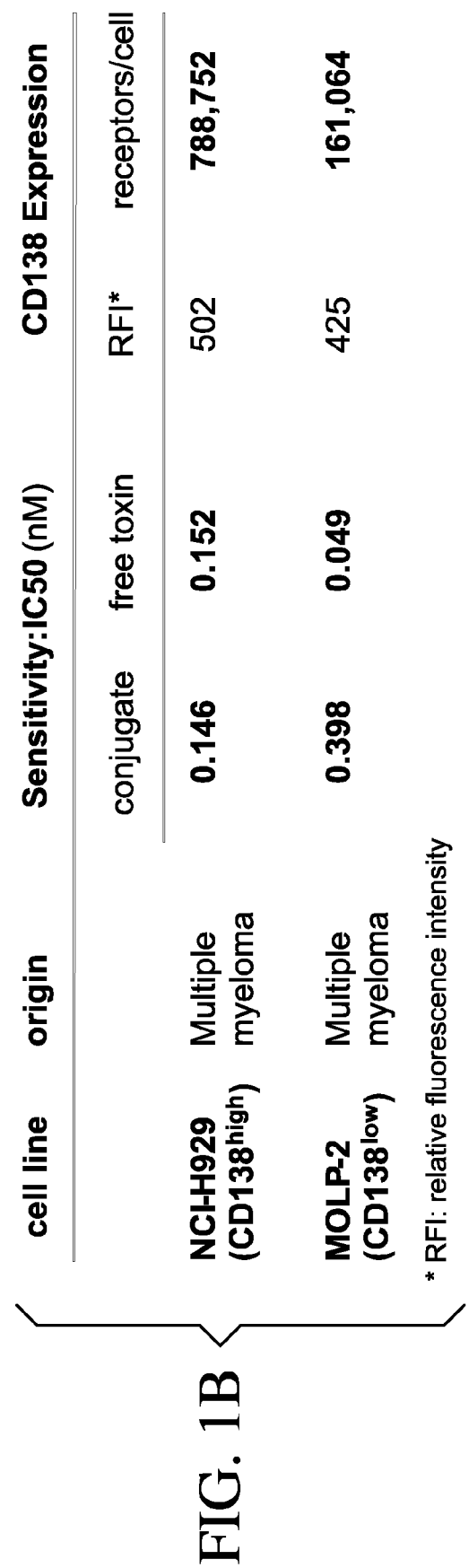

In FIG. 1B expression of CD138 on NCI-H929 (CD138$^{high}$) and MOLP-2 (CD138$^{low}$) model cells is shown. As can be seen the amount of CD138 receptors expressed on the surfaces of NCI-H929 cells relative to that expressed on MOLP-2 cells as measured by QIFIKIT generally correlates to the relative amount found on multiple myeloma cells relative to plasma cells, that is, tumor cells express significantly higher levels of CD138 than non-transformed (non-tumor) cells.

FIG. 1B also details the results of the cell viability assays described in the experimental section. The sensitivity of CD138$^{high}$ cells towards the CD138 specific immunoconjugate nBT062-SPDP-DM4 (expressed in terms of the IC$_{50}$ (nM)) is higher than the sensitivity of CD138$^{low}$ cells towards this immunoconjugate. On the other hand, the sensitivity of CD138$^{low}$ (MOLP-2) cells towards free DM4 is higher than that of the CD138$^{high}$ (NCI-H929) cells, with the sensitivity of the CD138$^{high}$ cells towards the free DM4 toxin (also expressed in terms of the IC$_{50}$ (nM)) almost equalling their sensitivity towards the immunoconjugate.

This forces the conclusion that the differences in the sensitivities CD138$^{high}$ and CD138$^{low}$ cells against the immunoconjugate are a specific property of the immunoconjugate and not just a reflection of reduced sensitivity of MOLP-2 cells against the effector molecule (here: DM4) of the immunoconjugate. The IC$_{50}$ values for both cell lines, CD138$^{high}$ and CD138$^{low}$, as provided in FIG. 1B, were calculated based on the dose response curves shown in FIGS. 2A and 3A.

Figure 1C:
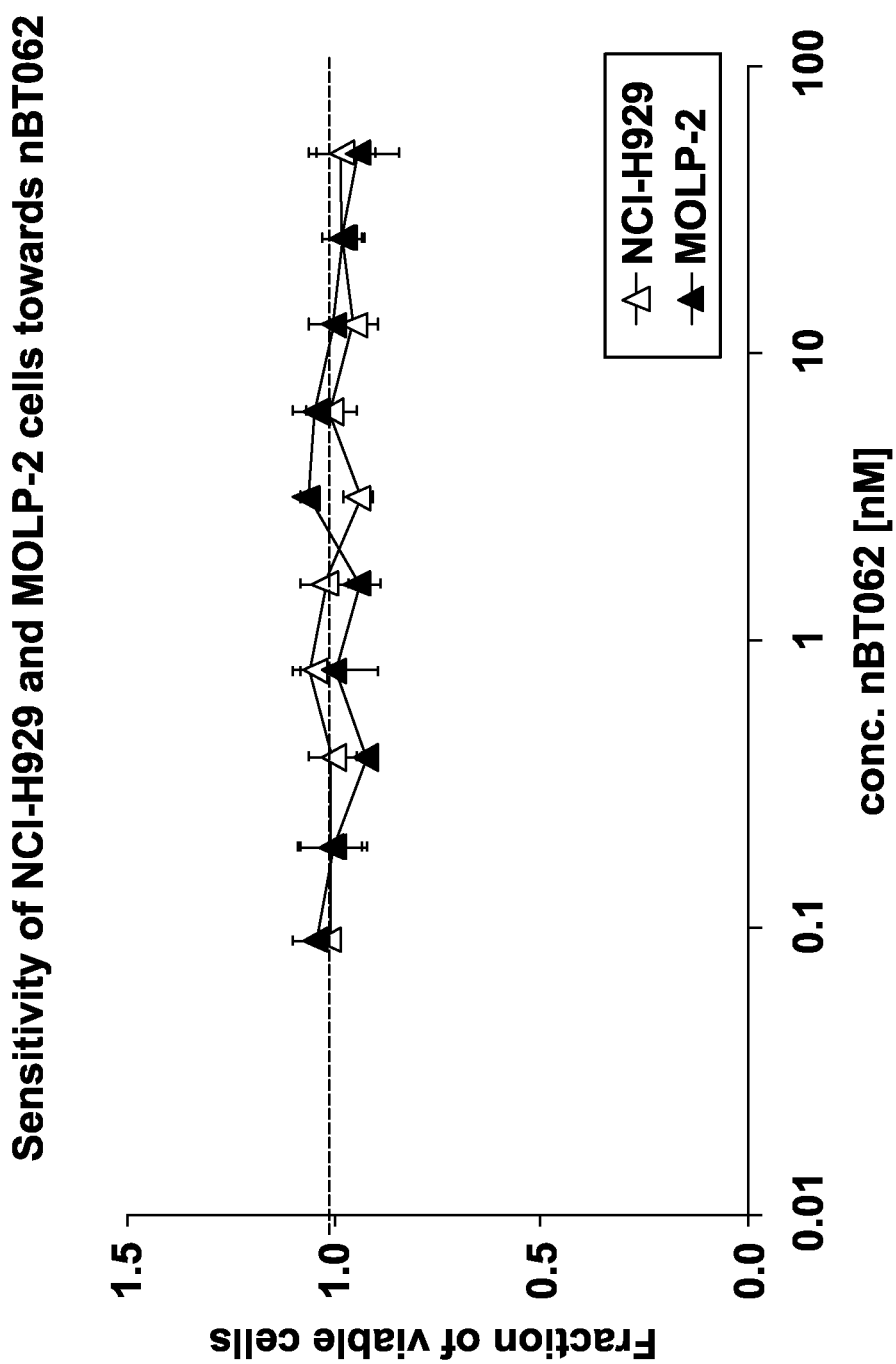

The impact of preincubation of CD138$^{high}$ and CD138$^{low}$ cells with an unconjugated targeting agent, here nBT062, was shown by the cell viability assays described in the experimental section. The fraction of viable cells was calculated in reference to untreated cells (set to 100% viable cells). FIG. 1C show the impact of incubation of unconjugated targeting agent (nBT062) by itself on MOLP-2 (CD138$^{low}$) and NCI-H929 (CD138$^{high}$) cells. The Figure makes clear that the unconjugated targeting agent used does not have an cytotoxic effect on either cell line.

Figure 2A:
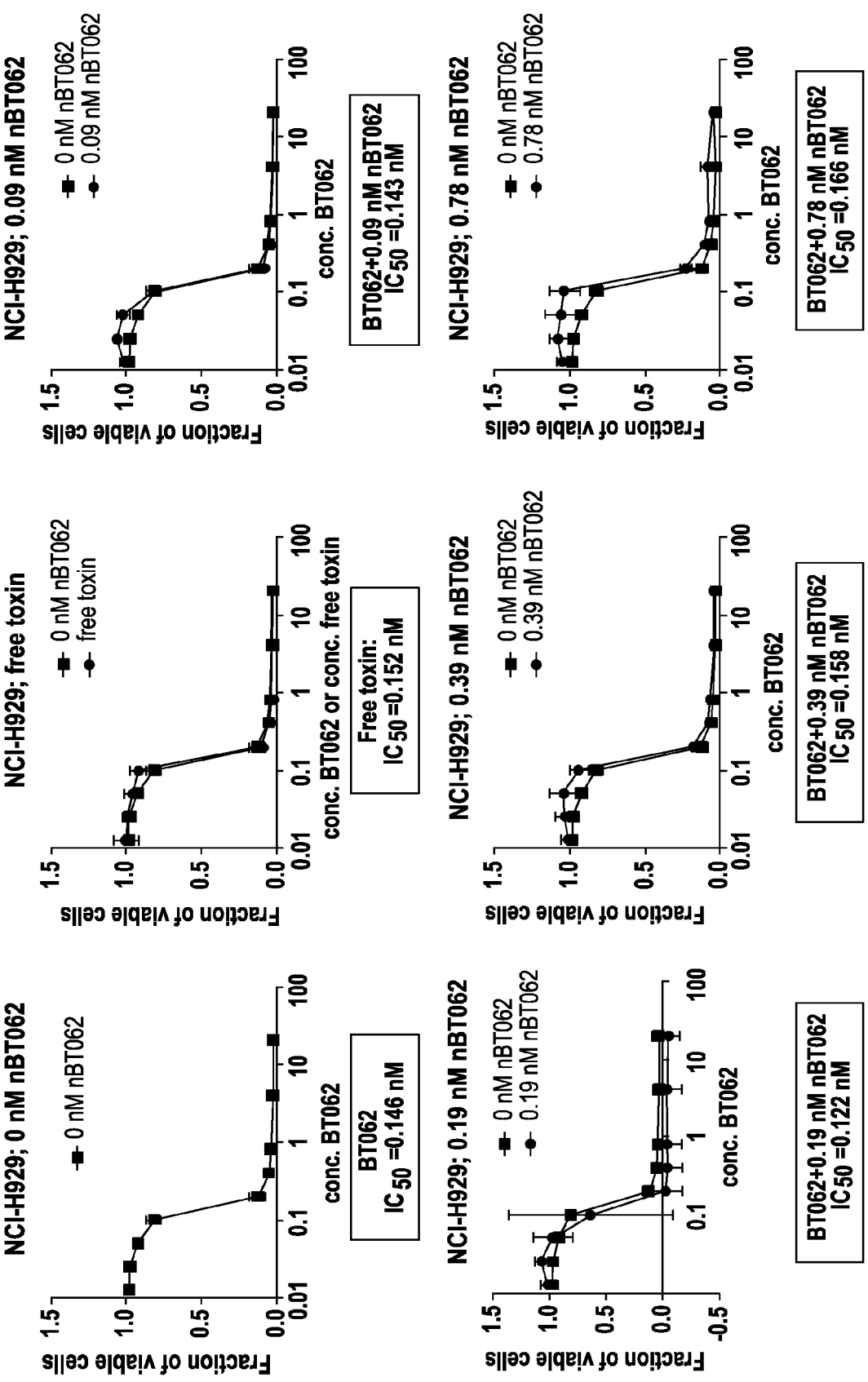
FIGS. 2 (A) and (B) depict the cytotoxicity of nBT062-SPDB-DM4 against NCI-H929 cells in the presence of increasing concentrations of nBT062. Each plot also shows the dose/response curve obtained in the absence of nBT062. Sensitivity of NCI-H929 cells against the free toxin is shown in (A) (second plot).
Figure 3A:
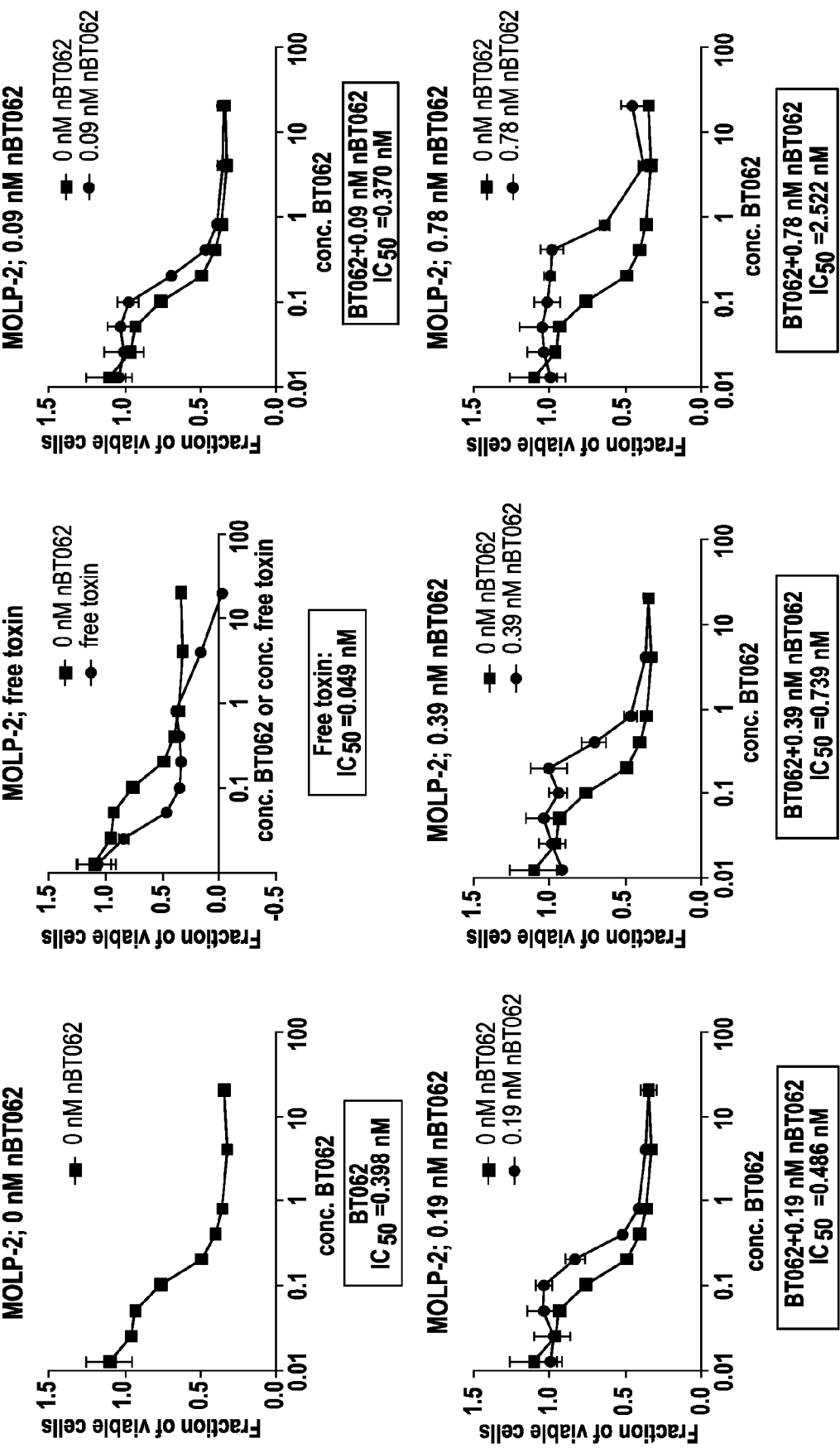
FIGS. 3 (A) and (B) depict the cytotoxicity of nBT062-SPDB-DM4 against MOLP-2 cells in the presence of increasing concentrations of nBT062. Each plot also shows the dose/response curve obtained in the absence of nBT062. Sensitivity of MOLP-2 cells against the free toxin is shown in (A) (second plot).
Figure 3B:
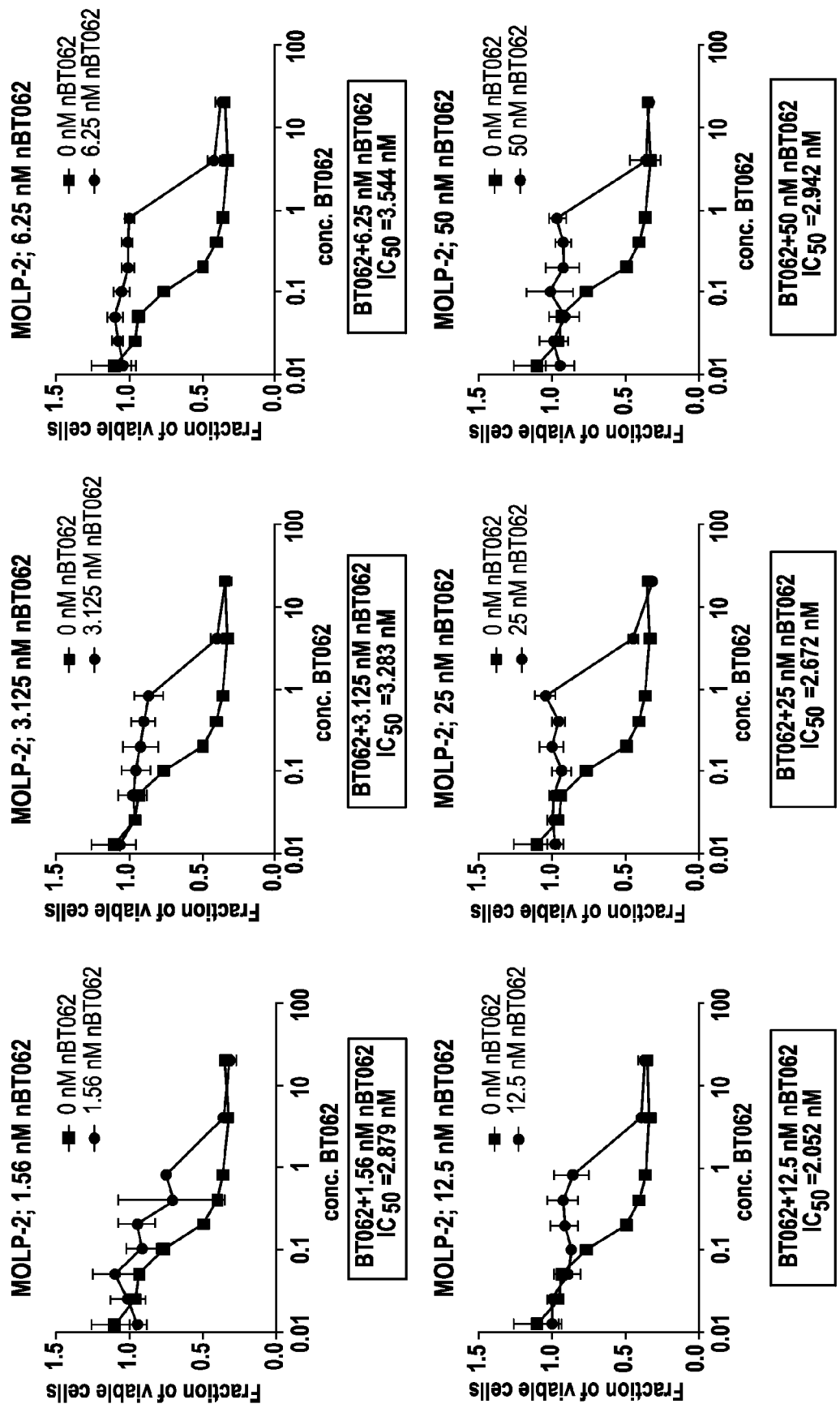
Figure 4:
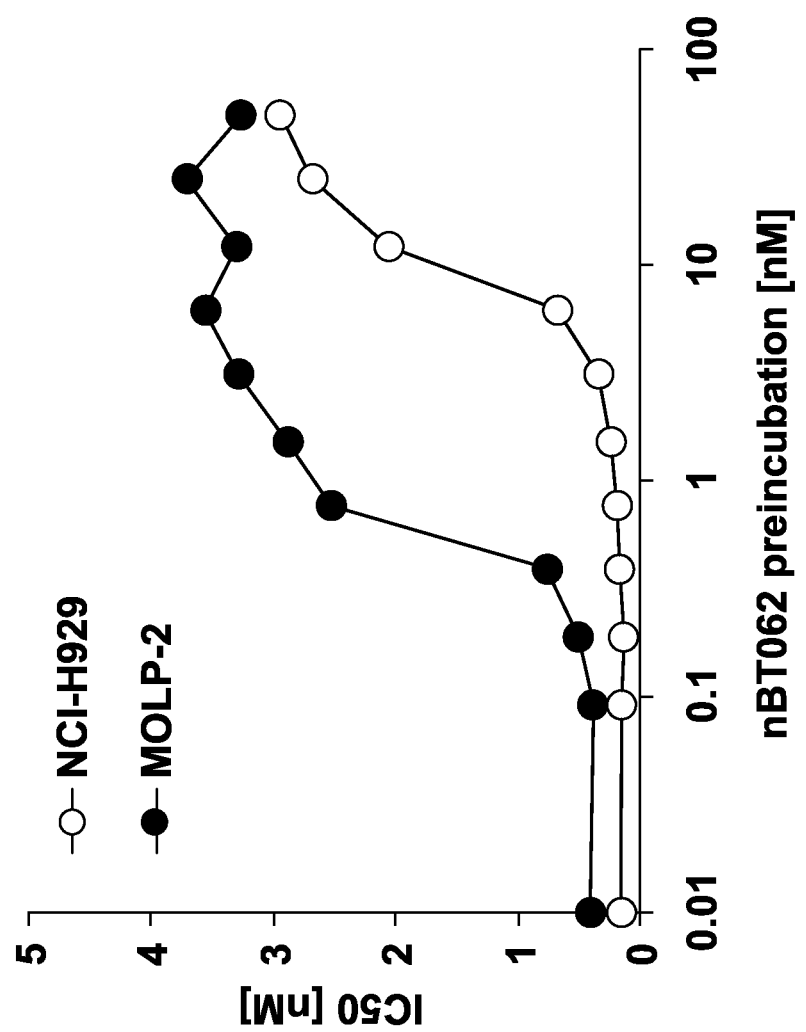
FIG. 4 depict the influence of increasing concentrations of nBT062 on the $IC_{50}$ values against NCI-H929 and MOLP-2 cells. The $IC_{50}$ values were calculated based on the dose-response curves shown in FIGS. 2 and 3 and plotted against the concentration of nBT062 used for preincubation.

FIG. 2A+B (NCI-H929 cells) and FIG. 3A+B (MOLP-2 cells) show the results of the different assays. Incubation, here preincubation for 30 min., of the cells with nBT062 at increasing concentrations reveals a protective effect for both cell lines. This shows that the unconjugated targeting agent, here nBT062, shields cell bound CD138, resulting in the decreased sensitivity of both cell lines against treatment with BT062. Increased concentrations of nBT062 thus led to an increase of IC$_{50}$ values for subsequently administered conjugate nBT062-SPDB-DM4 for both cell lines, that is, to a decrease of sensitivity towards this immunoconjugate. However and importantly, at equivalent concentrations of nBT062, the sensitivity of CD138$^{low}$ cells against subsequent nBT062-SPDB-DM4 treatment at a give concentration was significantly more reduced than the sensitivity of the CD138$^{high}$ cells. In FIG. 4, the IC$_{50}$ values for BT062 for both cell lines are plotted against the nBT062 concentration that was preadministered. As can be seen, at certain concentration ranges of nBT062 preadminsitered, for the MOLP-2 (CD138$^{low}$) cells, the nBT062 provides an effective shield against treatment with BT062, i.e., the IC$_{50}$ increases considerably, while in the same concentration ranges of nBT062, the NCI-H929 (CD138$^{high}$) remain highly sensitive to BT062. This concentration range of unconjugated targeting agent is of interest in the context of the present invention, as it represents the concentration range at which non-target cells are well protected, while target cells can still be effectively diminished.

As discussed above, to quantify the nBT062 mediated sensitivity reduction against the immunoconjugate, the degree of shielding (or more generically "sequestration") of both cell lines at a given concentration of nBT062 can calculated as described above.

IC$_{50}$ values as well as the sequestration values for both cell lines are provided in Table 1. The relative sequestration was calculated as described above. Values higher than 1 indicate that the shielding of CD138$^{low}$ cells is higher than that of CD138$^{high}$ cells for a given concentration of nBT062 (Table 1).

TABLE 1

IC$_{50}$ values of MOLP-2 and NCI-H929 cells in the absence or presence of different nBT062 concentrations. The reduction of sensitivity (increase of IC$_{50}$ value) calculated based on the formula below is given as % sequestration. The relative sequestration is calculated based on the protection values obtained on the individual cell lines for each nBT062 concentration (formula given below).

| | Sensitivity | | | | |
|---|---|---|---|---|---|
| nBT062 | MOLP-2; CD138$^{low}$ | | NCI-H929; CD138$^{high}$ | | |
| conc. (nM) | IC50 (nM) | sequestration[1] | IC50 (nM) | sequestration[1] | Relative sequestration[2] |
| — | 0.398 | — | 0.146 | — | — |
| 0.39 | 0.739 | 86% | 0.158 | 8% | 10.8 |
| 0.78 | 2.522 | 534% | 0.166 | 14% | 38.1 |
| 1.56 | 2.879 | 623% | 0.232 | 59% | 10.6 |
| 3.125 | 3.283 | 725% | 0.325 | 123% | 5.9 |

[1]sequestration = 100*(IC50 value with nBT062/IC50 value without nBT062) − 100
[2]relative sequestration = sequestation CD138$^{low}$/sequestation CD138$^{high}$ The results show that at certain concentrations of an unconjugated targeting agent, the relative sequestration is in fact significantly higher than 1. In the context of the present invention relative sequestration values of equal to or more than 10, equal to or more than 20, equal to or more than 30, equal to or more than 40 or equal to or more than 50 are preferred.

In Table 2, the viability of CD138$^{low}$ and CD138$^{high}$ cells after pre-treatment with an unconjugated targeting agent is shown relative to control cells that grew in the same concentration of unconjugated targeting agent. Both cell lines were treated with 0.4 or 0.8 nM of nBT062-SPDB-DM4 and either not pretreated (first row) or pretreated with increasing concentrations of nBT062. For example, at a concentration of 0.4 nM immunoconjugate, pre-treatment with 0.78 nM unconjugated targeting agent raised the viability of the model non-target cells from 41 to 99%, while the viability of the model target cells was only slightly increased from 6 to 10%. Thus, at a ratio of unconjugated targeting agent to immunoconjugate of 2:1, the goal of finding a ratio of unconjugated targeting agent to immunoconjugate that allows for a survival of the high percentile of CD138$^{low}$ (non target cells) and a low survival of CD138$^{high}$ cells (target cells) was almost optimally achieved. Thus, the data of Table 2 shows that by incubating the cells with certain concentrations of unconjugated targeting agent, CD138$^{low}$ (non-target cells) can be almost completely shielded from any effect of the immunoconjugate, that is, become close to or completely insensitive to subsequent immunoconjugate treatment, while the efficacy of BT062 against target cells is only slightly reduced.

TABLE 2

The percentages of viable cells (% of untreated control) for the individual cell lines are given as examples for given concentrations of BT062 and nBT062.

| BT062 conc. (nM) | nBT062 conc. (nM) | MOLP-2 Viable cells (% control) | NCI-H929 Viable cells (% control) | nBT062/BT062 ratio |
|---|---|---|---|---|
| 0.4 | — | 41 | 6 | — |
| 0.4 | 3.125 | 90 | 23 | 7.8 |
| 0.4 | 1.56 | 71 | 9 | 3.9 |
| 0.4 | 0.78 | 99 | 10 | 2.0 |
| 0.4 | 0.39 | 71 | 7 | 1.0 |
| 0.8 | — | 37 | 5 | — |
| 0.8 | 6.25 | 100 | 27 | 7.8 |
| 0.8 | 3.125 | 87 | 9 | 3.9 |
| 0.8 | 1.56 | 76 | 8 | 2.0 |

TABLE 2-continued

The percentages of viable cells (% of untreated control) for the individual cell lines are given as examples for given concentrations of BT062 and nBT062.

| BT062 conc. (nM) | nBT062 conc. (nM) | MOLP-2 Viable cells (% control) | NCI-H929 Viable cells (% control) | nBT062/BT062 ratio |
|---|---|---|---|---|
| 0.8 | 0.78 | 64 | 7 | 1.0 |
| 0.8 | 0.39 | 46 | 6 | 0.5 |

The acceptability of non-target cell destruction and/or target cell survival and thus the ratios of unconjugated targeting agent to immunoconjugate might vary from condition to condition, patient to patient (depending, e.g., on the overall condition or disease state of the patient) and the form and locus of administration (intravenous vs. contained injection into, e.g., a particular organ.

Accessibility of cells differs in place (locus of administration) and time (status of target cell treatment). Thus, differing accessibility of CD138 expressing non-tumor cells and CD138 expressing tumor cells, will, in certain embodiments, also contribute to results achieved with the method and composition of the present invention. For example, nBT062 may bind soluble CD138 and/or CD138 expressed on, at least certain types of, non-tumor cells, e.g., on cells floating in blood, more readily than CD138 expressed on tumor cells. At least a part of the later may, in certain embodiments of the invention, be relatively inaccessible to, e.g., nBT062. In certain embodiments, such relatively inaccessible CD138 will become more accessible during the course of the treatment as immunoconjugates cause apoptosis in cells. Subsequent to apoptosis the dead cells are removed, e.g. by phagocytosis, and access to previously inaccessible or hard to access tumor cells is provided.

"Sequestering" a substance, such as soluble or cell bound CD138, or a cell in the context of the present invention refers (i) to a binding of a substance or cell which diminishes or prevents further binding, in particular by immunoconjugates or (ii) to a physical separation of the substance or cell. A binding by, e.g., an unconjugated targeting agent to an individual CD138 antigen may reduce the affinity of the immunoconjugate to the individual CD138 antigen and may even render the individual CD138 unavailable for binding by an immunoconjugate targeting CD138. A reduction in affinity may, e.g., be the result of employing an unconjugated targeting agent that differs from the targeting agent of the immunoconjugate. For example, the unconjugated targeting agent may be a physiological CD138 ligand such as ADAMTS4 and the targeting agent of the immunoconjugate may be nBT062.

Thus, binding by, e.g., an unconjugated targeting agent may decrease non-tumor cell binding of the immunoconjugate. This will improve tumor targeting by protecting non-tumor cells from binding of an effective amount of immunoconjugate (also referred to herein "shielding" or "masking" of non-tumor cells) and thus decrease undesirable side effects associated with the administration of the immunoconjugates. The improved tumor targeting may be reflected by an increase in the effectiveness of a certain dosage of the immunoconjugate or alternatively, by the fact that a lower dosage can be employed to obtain an equivalent effect.

As discussed above, sequestering can also be solely based on a physical separation. For example, during plasmapheresis, plasma is separated from blood cells. Soluble antigen (e.g., sCD138) will be part of the plasma. At least part of the plasma may be replaced by a plasma expander, thus reducing the overall amount of soluble CD138 present. This will reduce the amount of non-tumor bound CD138 antigen available for binding by the immunoconjugate. As a result, e.g., the same dosage of immunoconjugate will result in a higher degree of binding to cell bound CD138 including a higher degree of binding to tumor cell bound CD138, than obtained without the sequestration by physical separation.

It is understood that a combination of sequestering based on binding and physical separation is also possible. For example, the sCD138 contained in plasma which is separated from blood cells during plasmapheresis may be bound, e.g., by the targeting agent, such as a CD138 specific adsorber and the plasma may be reintroduced into the patient. As outlined above, the present invention distinguishes between targeting agents that are functionally attached to an effector molecule (as part of an immunoconjugate) and unconjugated targeting agent. In the case of, e.g., a CD138 specific adsorber, the unconjugated targeting agent is attached to or associated with non-effector molecule(s) such as a matrix.

The unconjugated targeting agent and immunoconjugates according to the present invention can be administered by any route, including intravenously, parenterally, orally, intramuscularly, intrathecally or as an aerosol. The mode of delivery will depend on the desired effect. A skilled artisan will readily know the best route of administration for a particular treatment in accordance with the present invention. The appropriate dosage will depend on the route of administration and the treatment indicated, and can readily be determined by a skilled artisan in view of current treatment protocols.

Pharmaceutical compositions containing an unconjugated targeting agent and the immunoconjugate of the present invention as active ingredients can be prepared according to conventional pharmaceutical compounding techniques. See, for example, Remington's Pharmaceutical Sciences, 17th Ed. (1985, Mack Publishing Co., Easton, Pa.). Typically, effective amounts of active ingredients will be admixed with a pharmaceutically acceptable carrier. The carrier may take a wide variety of forms depending on the form of preparation desired for administration, for example, intravenous, oral, parenteral, intrathecal, transdermal, or by aerosol.

For oral administration, the unconjugated targeting agent and/or immunoconjugate can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent must be stable to passage through the gastrointestinal tract. If necessary, suitable agents for stable passage can be used, and may include phospholipids or lecithin derivatives described in the literature, as well as liposomes, microparticles (including microspheres and macrospheres).

For parenteral administration, the unconjugated targeting agent and/or the immunoconjugate may be dissolved in a pharmaceutical carrier and administered as either a solution or a suspension. Illustrative of suitable carriers are water, saline, phosphate buffer solution (PBS), dextrose solutions, fructose solutions, ethanol, or oils of animal, vegetative or synthetic origin. The carrier may also contain other ingredients, for example, preservatives, suspending agents, solubilizing agents, buffers and the like. When the unconjugated targeting agent and/or immunoconjugate are being administered intracerebroventricularly or intrathecally, they may also be dissolved in cerebrospinal fluid.

In accordance with the present invention, MM is treated as follows, with the use of nBT062 and BT062 as an example. This example is not intended to limit the present invention in any manner, and a skilled artisan could readily determine other unconjugated targeting agent and/or immunoconjugates that are within the scope of the present invention and other treatment regimes which could be utilized for the treatment of diseases such as MM. The two components are administered to a patient in need thereof at a ratio of 3:1 (nBT062/BT062) concomitantly. Due to the binding of nBT062 to tumor and non-tumor cells, the toxicity of BT062 towards non-tumor cells is reduced. In particular, the viability of the non-tumor cells is, at the specified amount of BT062 employed, increased by 40%, namely from 40% to 80%. Due to different factors such as a high expression of CD138 on patients' MM cells and/or the relative high turnover of CD138 on those cells, BT062 can bind, even after administration of nBT062, to tumor cells in an effective amount that will cause destruction of the tumor cells. In particular, the viability of the tumor cells is only increased by a couple of percentage points namely from 6% to 9%. Thus, the unconjugated targeting agent and the immunoconjugate of embodiments of this invention provide a means for the effective administration of the effector molecules to tumor cell sites where the effector molecules can be released from the immunoconjugate with clinically acceptable side effects. This targeted delivery and release provides a significant advance in the treatment of multiple myeloma.

The present invention is further described by reference to the following Examples, which are offered by way of illustration and are not intended to limit the invention in any manner. Standard techniques well known in the art or the techniques specifically described below are utilized.

EXPERIMENTAL SECTION

Material and Methods

Cell Lines

MOLP-2 is a human multiple myeloma cell line (DSMZ No.: ACC 607), which expresses CD138 in relatively low amounts (see details below and FIG. 1b). This cell line is also highly sensitive towards, e.g., the toxin DM4, indicating that its internal mechanisms to resist drug treatment are, if at all, underdeveloped. These facts underline that this cell line is an excellent model for non-target cells, in particular non-target $CD138^{low}$ cells.

NCI-H929 is a human multiple myeloma cell line (DSMZ No.: ACC 163), which expresses CD138 in, compared to MOLP-2 cells, relatively high amounts. (see details below and FIG. 1b). This cell line has also a high degree of resistance against free effector molecule, e.g., the toxin DM4, indicating that its internal mechanisms to resist drug treatment are, as in other tumor cells, well developed. These facts make this cell line an excellent model for tumor cells, in particular target $CD138^{high}$ cells as, e.g. found in multiple myeloma.

FACS Analysis for the Relative Determination of CD138 Expression $1 \times 10^5$ MOLP-2 and NCI-H929 multiple myeloma cells were each separately incubated with nBT062 to detect CD138 molecules on their cell surface. The cells were washed twice after addition of nBT062 antibody diluted in 100 µl PBS for 30 min at room temperature. Antibody concentrations used in this assay were 125-0.98 ng/ml. Bound antibody was detected upon subsequent incubation of the cells with 1/50 diluted FITC-conjugated goat anti-human IgG (Immunotech, Inc.) in PBS using a FACS Calibure flow cytometer (Beckton Dickinson). The FITC fluorescence was measured in the FL-1 channel. The mean fluorescence of untreated cells, isotype control treated cells and cells treated with the secondary antibody only were subtracted from the obtained values (mean value of controls). All determinations were performed in duplicate. The data for the determination of CD138 expression on the surface of NCI-H929 and MOLP-2 multiple myeloma cell lines by FACS analysis via unconjugated antibody nBT062 binding is shown in the histogram plots of FIG. 1A.

Determination of Absolute CD138 Receptor Numbers Via QIFIKIT

The QIFIKIT assay (DAKO USA) allows for the quantification of cell surface antigens by flow cytometry using an indirect immunofluorescence assay. This method was used to determine absolute receptor numbers of CD138 on the cell surface of MOLP-2 and NCI-H929 multiple myeloma cells. QIFIKIT consists of a series of 6 bead populations, approximately 10 µm in diameter and coated with different, but well-defined quantities of a mouse monoclonal antibody. The number of monoclonal antibody molecules on the 6 bead populations ranges from 0 to 400 000-800 000 and are provided with the kit. The beads mimic cells labeled with a specific primary mouse monoclonal antibody. Specimen cells were labeled with primary mouse Mab at saturating concentration. Under this condition the primary Mab is expected to bind to the respective cell surface antigen monovalently. Therefore, the number of bound antibody molecules corresponds to the number of antigenic sites. The cells are incubated at saturating concentration, in parallel with the QIFI-KIT beads, with Polyclonal Goat Anti-Mouse Immunoglobulins/FITC, Goat F(ab')$_2$.

A calibration curve was constructed by plotting the fluorescence intensity of the individual bead populations against the number of Mab molecules on the beads. The number of antigenic sites on the specimen cells were then determined by interpolation.

Cells ($1 \times 10^6$ cells/mL) in 50 µl/well were incubated for 45 min at 4° C. with different concentrations of nBT062 (125-0.98 ng/mL). Set up and calibration beads were prepared according to the manufacturer's recommendation. The wells were washed twice with 100 µl PBS. Bound nBT062 was detected using 100 µl FITC-conjugated secondary antibody (diluted 1:50 in PBS, incubation time 45 min, 4° C. in the dark).

Samples were analyzed by flow cytometry according to the manufacturer's recommendation.

The absolute receptor numbers of CD138 were quantified using the Qifikit is shown in FIG. 1B.

Cell Viability Assay

To assess the impact of preincubation of $CD138^{high}$ and $CD138^{low}$ cells with an unconjugated targeting agent, cell viability assays were performed.

NCI-H929 and MOLP-2 multiple myeloma cell lines were cultured in microtiter plates at a density of about 5000 cells/well. The cells were preincubated with unconjugated nBT062 at different concentrations for 30 min. Subsequently, cultures are treated with increasing concentrations of BT062. The cultures were incubated for 5 days before 10 µl of the tetrazolium salt containing WST-1 reagent (Roche) was added, followed by further incubation for 1-3 h to measure the cell viability. Color development due to formation of the formazan metabolite was quantified by determining the absorbance at 450 nm versus 690 nm (reference wavelength) in a microplate reader. Wells containing medium and WST-1 reagent served as blank control. The percentage of viable cells was calculated from the data obtained relative to data of cells grown in normal growth medium (set to 100%). In control exeriments, cells were treated under the same conditions with equimolar concentrations of free toxin or with unconjugated nBT062 and cell viability was measured as described above.

The above results are confirmed by the following co-culture experiments

Cell Viability in Co-Cultures

Cytotoxicity of BT062 towards CD138 expressing cells is measured by flow cytometry. About 2×10$^6$ cells expressing low levels of CD138 (non-target cells, CD138$^{low}$) are incubated for 5 min at room temperature (RT) with the fluorescent dye PKH67-GL (Sigma, Deisenhofen, Germany) according to the manufacturer's instructions. Incorporation of the dye is stopped by addition of heat-inactivated FBS. Then cells are washed twice with 15 ml of PBS.

Labelled cells are seeded together with unlabelled cells expressing high levels of CD138 ("target cells", CD138$^{high}$) in 96 well microtiter plates and incubated overnight at 37° C.

The cells are preincubated with different concentrations of unconjugated nBT062 in order to block a fraction of binding sites. In control samples, nBT062 is omitted. Subsequently, the cocultures are treated with increasing concentrations of BT062. After an additional incubation for 24-120 h, the cultures are transferred to polypropylene tubes. Cells are centrifuged for 5 min at 500•g, supernatant is removed and 200 µl/tube of a propidium iodide (PI) solution (1 µg/ml in PBS) is added. After incubation for 5-10 minutes at room temperature, fluorescence is determined by FACS analysis. The fraction of viable cells in reference to untreated cells is calculated using the CellQuestPro software (BD Biosciences). Viable CD138$^{low}$ cells are determined as PKH67-GL positive and PI negative. Viable CD138$^{high}$ cells (target cells) are determined as PKH67-GL negative and PI negative. Number of spontaneously lysed cells, measured in cultures that are treated identically but in the absence of BT062, are added. Alternatively, in another set of experiments, CD138$^{high}$ are labelled with PKH67-GL and coculturing is performed with unlabelled CD138$^{low}$ cells.

Decreasing Sensitivity of CD138$^{low}$ Non-Target Cells Towards BT062 Via nBT062 Preincubation The effect of preincubating the cells with unconjugated nBT062 on the viability of CD138$^{high}$ and CD138$^{low}$ cells is analyzed in coculture assays. CD138$^{low}$ cells are labelled with the fluorescent dye PKH67-GL before they are cocultured with unlabeled CD138$^{high}$ cells in order to allow differentiation of target and non-target cells in subsequent cell viability assays. Alternatively, CD138$^{high}$ cells are labelled with the same dye. Cocultures are treated with different concentrations of unconjugated nBT062 in order to partially block binding sites. Subsequently, BT062 is added to the cells and cell viability is analyzed by PI-staining and subsequent FACS analysis. The viability of non-target cells in cocultures after treatment with BT062 is increased by preincubation with the unconjugated antibody nBT062. Importantly, the efficacy of BT062 against target cells is only slightly reduced. This result further demonstrates that the cytotoxicity of BT062 towards CD138$^{low}$ non-target cells can be reduced by preincubation of the cells with nBT062, whereby the cytotoxicity of BT062 towards CD138$^{high}$ target cells is maintained.

Sequestration of Soluble CD138

Measurement of Soluble CD138 in Cell Culture Supernatants

Levels of soluble CD138 (sCD138) in cell culture supernatants of CD138 expressing cells are measured using a solid phase sandwich ELISA (Human CD138 ELISA kit, Diaclone, Besançon, France) according to the manufacturer's instructions.

Cell Viability Assay in Cultures Supplemented with sCD138

Soluble CD138 is purified from cell culture supernatants by antibody affinity chromatography using columns loaded with the anti-CD138 antibody B-B4 following standard procedures.

In order to obtain cell cultures of CD138 positive cells with known concentrations of sCD138 in their culture supernatant, media of freshly seeded cells are supplemented with different concentrations of purified sCD138. Cell culturing is performed in microtiter plates at a density of 5000 cells/well (for suspension cells) or at 900 cells/well (for adherent cells). The cells are preincubated with unconjugated nBT062 in order to block binding sites of sCD138. Subsequently, cultures are treated with increasing concentrations of BT062. The cultures are incubated for 1 to 5 days before 10 µl of the tetrazolium salt containing WST-1 reagent (Roche) is added, followed by further incubation for 1-3 h. Color development due to formation of the formazan metabolite is quantified by determining the absorbance at 450 nm versus 690 nm as reference wavelength in a microplate reader. Wells containing medium and WST-1 reagent serve as blank. The percentage of viable cells is calculated from these data relative to cells grown in normal growth medium (set to 100%).

Increasing Cytotoxic Activity of BT062 Towards CD138$^{high}$ Target Cells by Masking Soluble CD138 with nBT062

The cytotoxic activity of BT062 against CD138 expressing multiple myeloma cells is decreased by the presence of soluble CD138 in cell culture supernatants in vitro, by the presence of sCD138 in blood or tissues of multiple myeloma patients or in experimental animals in vivo. In order to prevent sCD138 to function as a competitor, nBT062 is used in an in vitro model system to block binding sites on sCD138. Therefore, CD138 expressing cells are cultured in microtiter plates with conditioned medium that contains sCD138 or in fresh cell culture medium supplemented with known concentrations of purified sCD138. Unconjugated nBT062 is added to the cultures prior or simultaneously to the addition of BT062. Cell viability is determined in WST-1 cell viability assays. The results show that the activity of BT062 can be enhanced by preincubation of the cells with nBT062, a result of masking of sCD138 binding sites with the unconjugated antibody nBT062.

Bibliography

Akkina R K, Rosenblatt J D, Campbell A G, Chen I S, Zack J A. Modeling human lymphoid precursor cell gene therapy in the SCID-hu mouse. Blood. 1994; 84:1393-1398.

Anttonen A, Heikkila P. Kajanti M, Jalkanen M, Joensuu H. High syndecan-1 expression is associated with favourable outcome in squamous cell lung carcinoma treated with radical surgery. Lung Cancer. 2001 June; 32(3):297-305.

Barbareschi M, Maisonneuve P, Aldovini D, Cangi M G, Pecciarini L, Angelo Mauri F, Veronese S, Caffo O, Lucenti A, Palma P D, Galligioni E, Doglioni C. High syndecan-1 expression in breast carcinoma is related to an aggressive phenotype and to poorer prognosis. Cancer. 2003 Aug. 1; 98(3):474-83.

Bernfield M, Kokenyesi R. Kato M, Hinkes M T, Spring J. Gallo R L, Lose E J. Biology of the syndecans: a family of transmembrane heparan sulfate proteoglycans. Annu Rev Cell Biol. 1992; 8:365-393.

Beste G, Schmidt F S, Stibora T, Skerra A. Small antibody-like proteins with prescribed ligand specificities derived from the lipocalin fold. Proc. Natl. Acad. Sci. USA. 1999: 96, 1898-1903.

Bhattacharyya B. Wolff J. Maytansine binding to the vinblastine sites of tubulin. FEBS Lett. 1977; 75:159-162.

Blättler W A and Chari R V J. Drugs to Enhance the Therapeutic Potency of Anticancer Antibodies: Antibody-Drug Conjugates as Tumor-Activated Prodrugs. In: Ojima, I., Vite, G. D. and Altmann, K.-H., Editors, 2001. Anticancer Agents-Frontiers in Cancer Chemotherapy, American Chemical Society, Washington, D.C., pp. 317-338.

Bross P F, Beitz J. Chen G. Chen X H, Duffy E, Kieffer L, Roy S. Sridhara R. Rahman A, Williams G. Pazdur R. Approval summary: gemtuzumab ozogamicin in relapsed acute myeloid leukemia. Clin Cancer Res. 2001; 7:1490-1496.

Carbone A, Gaidano G. Gloghini A, Ferlito A, Rinaldo A, Stein H. AIDS-related plasma-blastic lymphomas of the oral cavity and jaws: a diagnostic dilemma. Ann. 0 to 1. Rhinol. Laryngol. 1999; 108: 95-99.

Carter P. Improving the efficacy of antibody-based cancer therapies. Nat Rev Cancer. 2001; 1:118-129.

Chari R V, Martell B A, Gross J L, Cook S B, Shah S A, Blättler W A, McKenzie S J, Goldmacher V S. Immunoconjugates containing novel maytansinoids: promising anticancer drugs. Cancer Res. 1992; 52:127-131.

Chari R V, Jackel K A, Bourret L A, Derr S M, Tadayoni B M, Mattocks K M, Shah S A, Liu C, Blättler W A and Goldmacher V S. Enhancement of the selectivity and antitumor efficacy of a CC-1065 analogue through immunoconjugate formation. Cancer Res. 1995; 55: 4079-4084.

Charnaux N. Brule S. Chaigneau T. Saffar L, Sutton A, Hamon M, Prost C, Lievre N. Vita C, Gattegno L. RANTES (CCL5) induces a CCR5-dependent accelerated shedding of syndecan-1 (CD138) and syndecan-4 from HeLa cells and forms complexes with the shed ectodomains of these proteoglycans as well as with those of CD44. Glycobiology. 2004 Sep. 8 [Epub ahead of print]

Chen B P, Galy A, Kyoizumi S, Namikawa R, Scarborough J, Webb S, Ford B, Cen D Z, Chen S C. Engraftment of human hematopoietic precursor cells with secondary transfer potential in SCID-hu mice. Blood. 1994; 84:2497-2505.

Chilosi M, Adami F. Lestani M, Montagna L, Cimarosto L, Semenzato G, Pizzolo G, Menestrina F. CD138/syndecan-1: a useful immunohistochemical marker of normal and neoplastic plasma cells on routine trephine bone marrow biopsies. Mod Pathol. 1999; 12:1101-1106.

Clement C, Vooijs, W. C., Klein, B., and Wijdenes, J. In: al. SFSe, ed. J. Leukocyte Typing V. Oxford: Oxford University Press; 1995:714-715.

Couturier O, Faivre-Chauvet A; Filippovich I V; Thedréz P, Saï-Maurel C; Bardiés M; Mishra A K; Gauvrit M; Blain G; Apostolidis C; Molinet R; Abbe J C; Bateille R; Wijdenes J; Chatal J F; Cherel M; Validation of 213Bi-alpha radioimmunotherapy for multiple myeloma. Clinical Cancer Research 5(10 Suppl.) (October 1999) 3165s-3170s.

Davies E J et al., Blackhall F H, Shanks J H, David G, McGown A T, Swindell R. Slade R J, Martin-Hirsch P, Gallagher J T, Jayson G C, Distribution and Clinical Significance of Heparan Sulfate Proteoglycans in Ovarian Cancer Clin Cancer Res. 2004; 10(15):5178-86.

Dhodapkar M V, Abe E, Theus A, Lacy M, Langford J K, Barlogie B, Sanderson R D. Syndecan-1 is a multifunctional regulator of myeloma pathobiology: control of tumor cell survival, growth, and bone cell differentiation. Blood. 1998; 91:2679-2688.

Dore J M, Morard F, Vita N, Wijdenes J. Identification and location on syndecan-1 core protein of the epitopes of B-B2 and B-B4 monoclonal antibodies. FEBS Lett. 1998; 426:67-70.

Dowell J A, Korth-Bradley J, Liu H, King S P, Berger M S. Pharmacokinetics of gemtuzumab ozogamicin, an antibody-targeted chemotherapy agent for the treatment of patients with acute myeloid leukemia in first relapse. J Clin Pharmacol. 2001; 41:1206-1214.

Edinger M, Sweeney T J, Tucker A A, Olomu A B, Negrin R S, Contag C H. Noninvasive assessment of tumor cell proliferation in animal models. Neoplasia. 1999; 1:303-310.

Gattei V, Godeas C, Degan M, Rossi F M, Aldinucci D, Pinto A. Characterization of Anti-CD138 monoclonal antibodies as tools for investigating the molecular polymorphism of syndecan-1 in human lymphoma cells. Br J. Haematol. 1999; 104:152-162.

Hamann P R, Hinman L M, Beyer C F, Lindh D, Upeslacis J, Flowers D A, Bernstein I. An anti-CD33 antibody-calicheamicin conjugate for treatment of acute myeloid leukemia. Choice of linker. Bioconjug Chem. 2002; 13:40-46.

Han I, Park H, Oh E S. New insights into syndecan-2 expression and tumourigenic activity in colon carcinoma cells. J Mol. Histol. 2004: 35(3):319-26.

Horvathova M, Gaillard, J.-P., Liutard, J., Duperray, C., Lav-abre-Bertrand, T., Bourquard, P et al. In: al. SFSe, ed. Leucocyte Typing V. Oxford: Oxford University Press; 1995:713-714.

Krebs B, Rauchenberger R, Reiffert S, Rothe C, Tesar M, Thomassen E, Cao M, Dreier T, Fischer D, Hoss A et al. High-throughput generation and engineering of recombinant human antibodies. 2001. J. Immunol. Methods 254, pp. 67-84.

Kupchan S M, Sneden A T, Branfman A R, Howie G A, Rebhun L I, Mclvor W E, Wang R W, Schnaitman T C. Structural requirements for antileukemic activity among the naturally occurring and semisynthetic maytansinoids. J Med. Chem. 1978; 21:31-37.

Kyoizumi S. Baum C M, Kaneshima H, McCune J M, Yee E J, Namikawa R. Implantation and maintenance of functional human bone marrow in SCID-hu mice. Blood. 1992; 79:1704-1711.

Kyoizumi S, Murray L J, Namikawa R. Preclinical analysis of cytokine therapy in the SCID-hu mouse. Blood. 1993; 81:1479-1488.

Liu C, Tadayoni B M, Bourret L A, Mattocks K M, Derr S M, Widdison W C, Kedersha N L, Ariniello P D, Goldmacher V S, Lambert J M, Blättler W A, Chari R V. Eradication of large colon tumor xenografts by targeted delivery of maytansinoids. Proc Natl Acad Sci USA. 1996; 93:8618-8623.

McCune J M, Namikawa R, Kaneshima H, Shultz L D, Lieberman M, Weissman I L. The SCID-hu mouse: murine model for the analysis of human hematolymphoid differentiation and function. Science. 1988; 241:1632-1639.

Mennerich D, Vogel A, Klaman I, Dahl E, Lichtner R B, Rosenthal A, Pohlenz H D, Thierauch K H, Sommer A. Shift of syndecan-1 expression from epithelial to stromal cells during progression of solid tumours. Eur J. Cancer. 2004 June; 40(9):1373-82.

Mosmann T. Rapid colorimetric assay for cellular growth and survival: application to proliferation and cytotoxicity assays. J Immunol Methods. 1983; 65:55-63. Namikawa R, Ueda R, Kyoizumi S. Growth of human myeloid leukemias in the human marrow environment of SCID-hu mice. Blood. 1993; 82:2526-2536.

O'Connell F P, Pinkus J L, Pinkus G S. CD138 (Syndecan-1), a Plasma Cell Marker Immunohistochemical Profile in Hematopoietic and Nonhematopoietic Neoplasms. Am J Clin Pathol 2004; 121:254-263.

Ojima I, Geng X, Wu X, Qu C, Borella C P, Xie H, Wilhelm S D, Leece B A, Bartle L M, Goldmacher V S and Chari R V. Tumor-specific novel taxoid-monoclonal antibody conjugates. 2002. J. Med. Chem. 45, pp. 5620-5623.

Olafsen, T, Cheung, C C, Yazaki, P J, Li L, Sundaresan G, Gambhir S S, Sherman, M A, Williams, L E, Shively, J E, Raubitschek, A A, and Wu, A M. Covalent disulfide-linked anti-CEA diabody allows site-specific conjugation and radiolabeling for tumor targeting applications. 2004; Prot. Eng. Design & Selection 17:1: 21-27.

Orosz Z, Kopper L. Syndecan-1 expression in different soft tissue tumours. Anticancer Res. 2001: 21 (1B):733-7.

Padlan, E A. A possible procedure for reducing the immunogenicity of antibody variable domains while preserving their ligand-binding properties. Mol. Immunol. 1991; 28: 489-498.

Payne G. Progress in immunoconjugate cancer therapeutics. Cancer Cell. 2003; 3:207-212.

Pegram M D, Lipton A, Hayes D F, Weber B L, Baselga J M, Tripathy D, Baly D, Baughman S A, Twaddell T. Glaspy J A and Slamon D J. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. 1998. J. Clin. Oncol. 16, pp. 2659-2671.

Rawstron A C, Owen R G, Davies F E, Johnson R J, Jones R A, Richards S J, Evans P A, Child J A, Smith G M, Jack A S, Morgan G J. Circulating plasma cells in multiple myeloma: characterization and correlation with disease stage. Br J. Haematol. 1997; 97:46-55.

Remillard S, Rebhun L I, Howie G A, Kupchan S M. Antimitotic activity of the potent tumor inhibitor maytansine. Science. 1975; 189:1002-1005.

Roh Y H, Kim Y H, Choi H J, Lee K E, Roh M S. Syndecan-1 Expression in Gallbladder Cancer and Its Prognostic Significance, Eur Surg Res 2008; 41:245-250.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994; 91:969-973.

Ross S, Spencer S D, Holcomb I, Tan C, Hongo J, Devaux B, Rangell L, Keller G A, Schow P, Steeves R M, Lutz R J, Frantz G, Hillan K, Peale F, Tobin P, Eberhard D, Rubin M A, Lasky L A, Koeppen H. Prostate stem cell antigen as therapy target: tissue expression and in vivo efficacy of an immunoconjugate. Cancer Res. 2002 May 1; 62(9):2546-53.

Ross J S, Gray K, Gray G, Worland P J, Rolfe M. Anticancer Antibodies, Am J Clin Path. (Apr. 17, 2003).

Sanderson R D, Lalor P. Bernfield M. B lymphocytes express and lose syndecan at specific stages of differentiation. Cell Regul. 1989; 1:27-35.

Sandhu J S, Clark B R, Boynton E L, Atkins H, Messner H, Keating A, Hozumi N. Human hematopoiesis in SCID mice implanted with human adult cancellous bone. Blood. 1996; 88:1973-1982.

Sasaki A, Boyce B F, Story B, Wright K R, Chapman M, Boyce R, Mundy G R, Yoneda T. Bisphosphonate risedronate reduces metastatic human breast cancer burden in bone in nude mice. Cancer Res. 1995; 55:3551-3557.

Schneider U. van Lessen A, Huhn D, Serke S. Two subsets of peripheral blood plasma cells defined by differential expression of CD45 antigen. Br J. Haematol. 1997; 97:56-64.

Sebestyen A, Berczi L, Mihalik R, Paku S, Matolcsy A, Kopper L. Syndecan-1 (CD138) expression in human non-Hodgkin lymphomas. Br J. Haematol. 1999; 104(2):412-9.

Seftalioglu A, Karakus S. Syndecan-1/CD138 expression in normal myeloid, acute lymphoblastic and myeloblastic leukemia cells. Acta Histochem. 2003; 105:213-221.

Seftalioglu A, Karakus S, Dundar S, Can B, Erdemli E, Irmak M K, Oztas E, Korkmaz C, Yazar F, Cavusoglu I. Syndecan-1 (CD138) expression in acute myeloblastic leukemia cells—an immuno electron microscopic study. Acta Oncol. 2003; 42:71-74.

Senter P D, Doronina S. Cerveny C, Chace D, Francisco J, Klussman K, Mendelsohn B, Meyer D, Siegall C B, Thompson J et al. (2002). Cures and regressions of established tumors with monoclonal antibody auristatin conjugates. Abstract #2062, American Assoication for Cancer Res. (San Francisco, Calif.: American Association for Cancer Res.), 414.

Sievers E L, Larson R. A., Stadtmauer, E. A., Estey, E., Lowenberg, B., Dombret, H., Karanes, C., Theobald, M., Bennett, J. M., Sherman, M. L. et al. Efficacy and safety of gemtuzumab ozogamicin in patients with CD33-positive acute myeloid leukemia in first relapse. 2001. J. Clin. Oncol. 19, pp. 3244-3254.

Sievers E L and Linenberger M. Mylotarg: antibody-targeted chemotherapy comes of age. 2001. Curr. Opin. Oncol. 13, pp. 522-527.

Smith R., Single chain antibody variable region fragments; available at the Stanford University website (last updated on May, 2001).

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994: 7(6): 805-814.

Tassone P, Goldmacher V S, Neri P, Gozzini A, Shammas M A, Whiteman K A, Hylander-Gans L L, Carrasco D R, Hideshima T, Shringarpure R, Shi J, Allam C K, Wijdenes J, Venuta S, Munshi N C, Anderson K C, Cytotoxic activity of the maytansinoid immunoconjugate B-B4-DM1 against CD138+ multiple myeloma cells, Blood, 2004, 104 (12), pp. 3688-3696.

Tolcher A W, Ochoa L, Hammond L A, Patnaik A, Edwards T, Takimoto C, Smith L, de Bono J, Schwartz G, Mays T, Jonak Z L, Johnson R, DeWitte M, Martino H, Audette C, Maes K, Chari R V, Lambert J M, Rowinsky E K. Cantuzumab mertansine, a maytansinoid immunoconjugate directed to the CanAg antigen: a phase 1, pharmacokinetic, and biologic correlative study. J Clin Oncol. 2003; 21:211-222.

Urashima M, Chen B P, Chen S, Pinkus G S, Bronson R T, Dedera D A, Hoshi Y, Teoh G, Ogata A, Treon S P, Chauhan D, Anderson K C. The development of a model for the homing of multiple myeloma cells to human bone marrow. Blood. 1997; 90:754-765.

Vogel C W. Preparation of immunoconjugates using antibody oligosaccharide moieties. Methods in Molecular Biology: Bioconjugation protocols strategies and methods. 2004; 283:087-108.

Vooijs W C, Post J. Wijdenes J, Schuurman H J, Bolognesi A, Polito L, Stirpe F, Bast E J, de Gast G C. Efficacy and toxicity of plasma-cell-reactive monoclonal antibodies B-B2 and B-B4 and their immunotoxins. Cancer Immunol Immunother. 1996; 42:319-328.

Ward, E. S., D. Gussow, A. D. Griffiths, P. T. Jones, and G. Winter. Binding activities of a repertoire of single immunoglobin variable domains secreted from *Escherichia coli*. Nature. 1989. 341:544-546.

Wargalla U C, Reisfeld R A. Rate of internalization of an immunotoxin correlates with cytotoxic activity against human tumor cells. Proc. Natl. Acad. Sci. USA. 1989; 86:5146-5150.

Wijdenes J. Vooijs W C, Clement C, Post J, Morard F, Vita N, Laurent P, Sun R X, Klein B, Dore J M. A plasmocyte selective monoclonal antibody (B-B4) recognizes syndecan-1. Br J. Haematol. 1996; 94:318-323.

Wijdenes J, Dore J M, Clement C, Vermot-Desroches C. CD138, J Biol Regul Homeost Agents. 2002 April-June; 16(2):152-5.

Witzig T E, Kimlinger T K, Ahmann G J, Katzmann J A, Greipp P R. Detection of myeloma cells in the peripheral blood by flow cytometry. Cytometry. 1996; 26:113-120.

Xie H, Audette C, Hoffee M, Lambert J M, Blättler W. Pharmacokinetics and biodistribution of the antitumor immunoconjugate, cantuzumab mertansine (huC242-DM1), and its two components in mice. J Pharmacol Exp Ther. 2004 March; 308(3):1073-82.

Yang M, Jiang P, An Z, Baranov E, Li L, Hasegawa S, Al-Tuwaijri M, Chishima T, Shimada H, Moossa A R, Hoffman R M. Genetically fluorescent melanoma bone and organ metastasis models. Clin Cancer Res. 1999; 5:3549-3559.

Yang M, Baranov E, Jiang P, Sun F X, Li X M, Li L, Hasegawa S, Bouvet M, Al-Tuwaijri M, Chishima T, Shimada H, Moossa A R, Penman S, Hoffman R M. Whole-body optical imaging of green fluorescent protein-expressing tumors and metastases. Proc Natl Acad Sci USA. 2000; 97:1206-1211.

What is claimed is:

1. A method for improving tumor targeting, of immunoconjugates targeting cell bound CD138 antigen expressed on target cells comprising:
   (a) administering to a patient in need thereof an unconjugated antibody, wherein said unconjugated antibody binds to a linear epitope between residues 90-95 of the core protein on human CD138 wherein CD138 is, in the blood of said patient, cell bound on target cells and non-target cells and is also present in soluble form (soluble antigen) and wherein said target cells are cancer cells and;
   (b) sequestering in said patient cell bound CD138 antigen on target and non-target cell, optionally soluble antigen, and optionally CD138 antigen expressing cells, wherein the cell bound CD138 antigen and soluble CD138 antigen are different configurations of the same CD138 antigen,
   (c) administering an immunoconjugate targeting said cell bound CD138 antigen expressed on target cells comprising a targeting antibody for said cell bound CD138 antigen that is functionally attached to an effector molecule, wherein said sequestering in (b) improves tumor targeting of said immunoconjugate.

2. The method of claim 1, wherein the unconjugated antibody sequesters said cell bound CD138 antigen, soluble antigen and/or said antigen expressing cells.

3. The method of claim 1, wherein the cell bound CD138 antigen is internalized upon binding to the immunoconjugate and/or is subject to shedding.

4. The method of claim 1, wherein said non-target cells comprise not readily regenerating cells.

5. The method of claim 2, wherein a relative sequestration of CD138 expressing non-target cells to CD138 expressing target cells is higher than 5 or higher than 10.

6. The method of claim 2, wherein a ratio of the unconjugated antibody to the immunoconjugate provided is about 10:1 to about 1:2.

7. The method of claim 2, wherein a vasodilatory agent is provided prior to or concomitant with the unconjugated antibody.

8. The method of claim 1, wherein said immunoconjugate targeting cell bound CD138 is administered concurrently with or subsequent to said unconjugated CD138 antibody.

9. The method of claim 8, wherein said sequestering in (b) and administering in (c) is separated by a time interval.

10. The method of claim 9, wherein the time interval is at least 20 minutes.

11. The method of claim 1, wherein said targeting antibody in (c) is antibody B-B4.

12. The method of claim 1, wherein said unconjugated antibody is nBT062.

13. The method of claim 4, wherein the not readily regenerating cells are epithelial cells, brain, heart, kidney or liver cells.

14. The method of claim 7, wherein the vasodilatory agent is prazosin, terazosin or doxazosin.

15. The method of claim 1, wherein said targeting antibody comprises HCDR1, HCDR2 and HCDR3 and LCDR1, LCDR2 and LCDR3 of the B-B4 antibody.

16. The method of claim 1, wherein said non-target cells are epithelial cells or liver cells.

17. The method of claim 5, wherein the relative sequestration of CD138 expressing non-target cells to CD138 expressing target cells obtained is higher than 20 or higher than 30.

18. The method of claim 6, wherein the ratio of the unconjugated antibody to the immunoconjugate provided is about 5:1 to 2:1.

* * * * *